(12) United States Patent
Kim et al.

(10) Patent No.: US 11,464,715 B2
(45) Date of Patent: Oct. 11, 2022

(54) INGESTIBLE TABLET OR POWDER TYPE ORAL CLEANING COMPOSITION

(71) Applicant: Bareun Co., Ltd., Chuncheon-si (KR)

(72) Inventors: Han Soo Kim, Chuncheon-si (KR); Byung Hee Chung, Chuncheon-si (KR)

(73) Assignee: Bareun Co., Ltd., Chuncheon-si (KR)

( * ) Notice: Subject to any disclaimer, the term of this patent is extended or adjusted under 35 U.S.C. 154(b) by 0 days.

(21) Appl. No.: 17/076,065

(22) Filed: Oct. 21, 2020

(65) Prior Publication Data

US 2021/0299001 A1 Sep. 30, 2021

(30) Foreign Application Priority Data

Feb. 28, 2020 (KR) .................. 10-2020-0024742

(51) Int. Cl.
| | | |
|---|---|---|
| *A61Q 11/00* | (2006.01) | |
| *A61K 8/02* | (2006.01) | |
| *A61K 8/9778* | (2017.01) | |
| *A61K 8/25* | (2006.01) | |
| *A61K 8/34* | (2006.01) | |
| *A61K 8/36* | (2006.01) | |
| *A61K 8/66* | (2006.01) | |
| *A61K 8/73* | (2006.01) | |
| *A61K 8/92* | (2006.01) | |

(52) U.S. Cl.
CPC ............ *A61K 8/022* (2013.01); *A61K 8/0245* (2013.01); *A61K 8/25* (2013.01); *A61K 8/345* (2013.01); *A61K 8/361* (2013.01); *A61K 8/66* (2013.01); *A61K 8/738* (2013.01); *A61K 8/927* (2013.01); *A61K 8/9778* (2017.08); *A61Q 11/00* (2013.01); *A61K 2800/59* (2013.01); *A61K 2800/92* (2013.01)

(58) Field of Classification Search
CPC .. A61K 2300/00; A61K 8/60; A61K 2800/92; A61K 9/006; A61K 8/022; A61K 35/744; A61K 2800/59; A61Q 11/00; A61Q 17/005

See application file for complete search history.

(56) References Cited

U.S. PATENT DOCUMENTS

| | | |
|---|---|---|
| 2004/0258733 A1 | 12/2004 | Maxwell et al. |
| 2007/0110683 A1* | 5/2007 | Levine .................. A61K 8/676 424/58 |
| 2010/0166812 A1* | 7/2010 | Nam .................. A61Q 11/00 424/401 |
| 2012/0141386 A1 | 6/2012 | Huang et al. |
| 2014/0227202 A1* | 8/2014 | Pilgaonkar ............. A61Q 11/00 424/52 |
| 2015/0044266 A1* | 2/2015 | Fetissova ........... A61K 38/4873 424/401 |
| 2015/0208703 A1* | 7/2015 | Turner ................ A23L 27/34 426/548 |

FOREIGN PATENT DOCUMENTS

| | | | |
|---|---|---|---|
| CN | 110623879 A | | 12/2019 |
| JP | 2001089344 A | * | 4/2001 |
| JP | 2007-501273 A | | 1/2007 |
| JP | 2014-508136 A | | 4/2014 |
| KR | 10-0203733 B | | 6/1999 |
| KR | 10-2005-0029905 A | | 3/2005 |
| KR | 10-2009-0076440 A | | 7/2009 |
| KR | 10-2009-0076443 A | | 7/2009 |
| KR | 10-2012-0054506 A | | 5/2012 |
| KR | 10-2015-0027352 A | | 3/2015 |
| KR | 10-2015-0132654 A | | 11/2015 |
| KR | 10-1914491 B1 | | 11/2018 |
| KR | 10-1985771 B1 | | 6/2019 |
| KR | 10-2019-0094009 A | | 8/2019 |

OTHER PUBLICATIONS

Blog Posting about Recommendation of Mouthwash; https://blog.naver.com/eunsucks/140210195851.
Office Action dated Jun. 3, 2022 from the Japanese Patent Office (JPO) for Japanese Patent Application No. 2020-177146.
"OraMoist Time Released Dry Mouth Discs", ID 1095522, Mintel GNPD[online], retrieved May 2009, URL: https://www.portal.mintel.com, 7 pages total.
"Xylitol Salmiac Mints", ID 579705, Mintel GNPD[online], retrieved 2006, URL: https://www.portal.mintel.com, 5 pages total.

* cited by examiner

*Primary Examiner* — Tracy Liu
(74) *Attorney, Agent, or Firm* — Sughrue Mion, PLLC

(57) ABSTRACT

An oral cleaning composition in ingestible tablet or powder formulation contains natural materials. It has an advantage of portability because it is provided in a tablet or powder form instead of a liquid or gel form. In addition, the composition does not contain synthetic chemical components but uses only natural materials and can be safely ingested after use, and, thus, it does not require a space where it can be spit out. Furthermore, it exhibits excellent efficacy in inhibiting oral bacteria and removing bad breath.

13 Claims, 31 Drawing Sheets

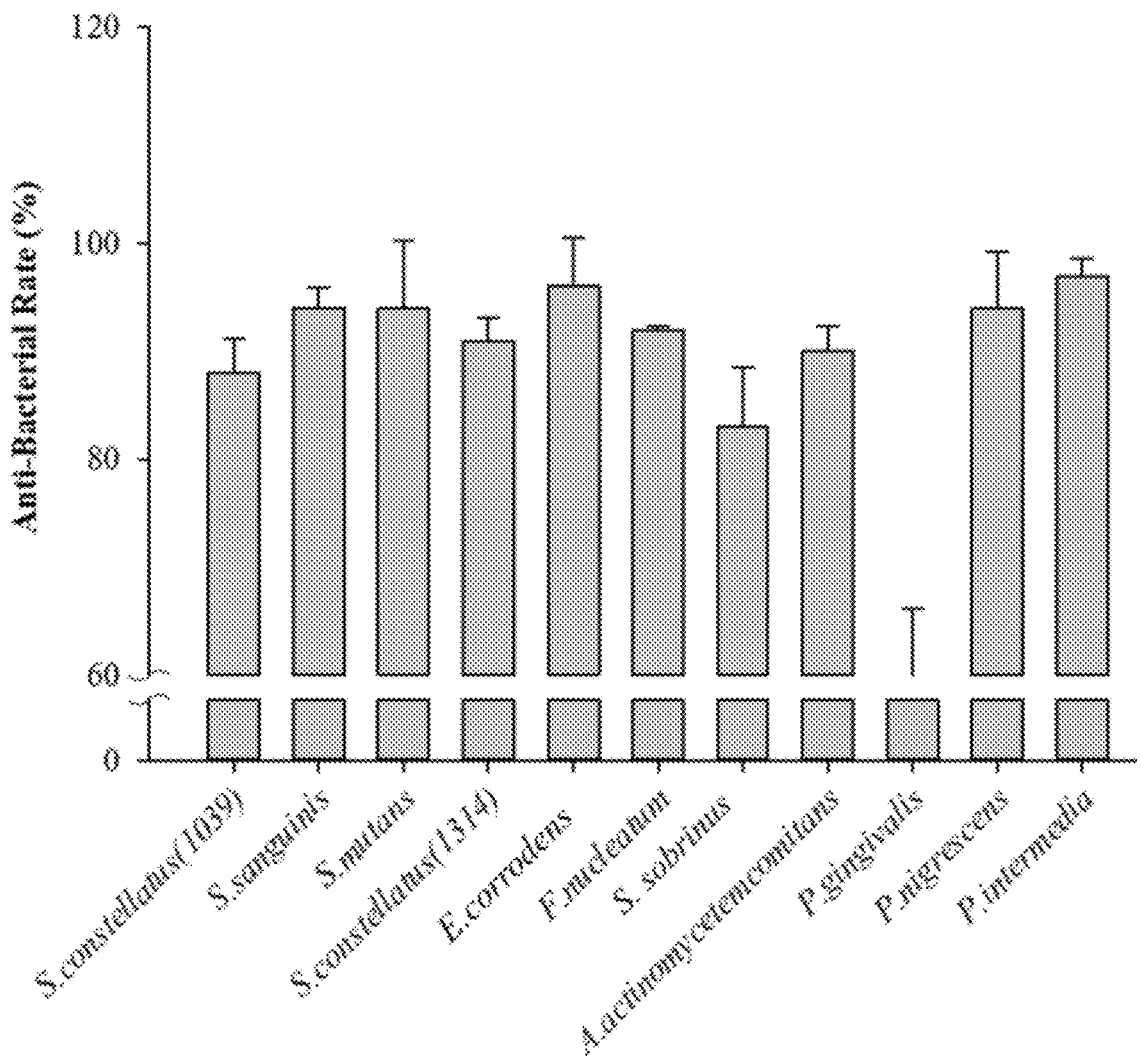

INGESTIBLE TABLET OR POWDER TYPE ORAL CLEANING COMPOSITION

CROSS REFERENCE TO RELATED APPLICATIONS

This application claims priority to Korean Patent Application No. 10-2020-0024742, filed Feb. 28, 2020, the contents of all of which are incorporated herein by reference in their entirety.

TECHNICAL FIELD

The present invention relates to an ingestible tablet or powder type oral cleaning composition, and more particularly, to a tablet or powder type oral cleaning composition which can be ingested because it is composed of only natural ingredients, and is capable of inhibiting bacteria and odors in an oral cavity.

BACKGROUND ART

An oral cavity, which is a main organ for breathing and food intake, is constantly exposed to external antigens through air and food, and therefore, if the oral cavity is not kept clean through brushing, etc., a dental plaque is created at the periphery of teeth and gums (gingiva), and the created dental plaque is gradually calcified to form a dental calculus on a surface of the tooth. The dental plaque and calculus have very important pathological significance in that they become a proliferation point of oral bacteria and cause gum inflammatory diseases such as gingivitis and periodontitis.

Dental caries and periodontal diseases are oral diseases which are a problem worldwide with regard to oral health. According to a recent WHO report, the dental caries and periodontal diseases have been reported to occur in about 60% of the world's adult population, and the primary cause of such oral disease is known to be bacteria present in a tooth surface bacterial film.

Bacteria causing the dental caries include *streptococcus* of the *mutans* group (*mutans streptococcus*) such as *Streptococcus mutans* and *Staphylococcus sobrinus*. Most of the bacteria related to periodontal disease are Gram-negative anaerobic bacterial species present in a subgingival tooth surface bacterial film and include *Porphyromonas gingivalis, Fusobacterium nucleatum, Prevotella intermedia, Eikenella corrodens, Actinobacillus actinomycetemcomitans, Bacteroides* forsythus, Campybacterrectus, *Treponema*, etc.

Microorganisms in the oral cavity attach to the tooth surface to form a bacterial film, and thus, in order to prevent periodontal disease or inhibit the progression of periodontal disease, a physical method such as brushing or flossing, or a chemical method such as antibiotics or oral cleaning together with the physical method may be used. Among them, the oral cleaning is widely used as an easy-to-use oral hygiene product.

Prior patent documents for the oral cleaning include Korean Laid-open Patent Publication Nos. 1994-8669, 1995-16696, 2002-28765 and 2004-66313. These are inventions directed to the oral cleaning comprising some herbal ingredients, and only describe the whitening effect of teeth, but do not describe the action of inhibiting bacteria in the teeth.

In addition, conventional oral cleaning products have a problem in that they are usually provided in a liquid or gel form and thus, are inconvenient to carry, and further, they must be spit out after washing with a gargle or toothbrush in the mouth and thus, need a space where they can be spit out, i.e., a toilet, a sink, etc.

DISCLOSURE

Technical Problem

The present invention has been conceived to solve the above problems, and an object of the present invention is to provide an oral cleaning composition which is composed of a tablet or powder type formulation and thus is easy to carry and ingest; includes only natural materials and thus can be ingested; and has an excellent effect of removing bacteria and bad breath in an oral cavity.

Technical Solution

In order to achieve the above object, the present invention provides a tablet or powder type oral cleaning composition comprising: 3 to 10% by weight of salt, 40 to 70% by weight of xylitol, 0.5 to 15% by weight of bellflower, 0.1 to 15% by weight of quince and 10 to 15% by weight of mint, based on the weight of the total composition.

The composition of the present invention may further comprise: 1 to 20% by weight of lemon, 5 to 20% by weight of green tea, 0.01 to 0.5% by weight of propolis, and 0.01 to 0.5% by weight of monk fruit, based on the weight of the total composition.

The composition of the present invention may further comprise: 0.1 to 5% by weight of magnesium stearate and 0.1 to 5% by weight of silicon dioxide, based on the weight of the total composition, and may be a tablet type formulation.

The composition of the present invention may further comprise 1 to 5% by weight of maltodextrin based on the weight of the total composition, and may be a powder type formulation.

The present invention also provides a tablet type oral cleaning composition comprising: 4 to 7% by weight of salt, 45 to 60% by weight of xylitol, 0.5 to 2.0% by weight of bellflower, 0.2 to 2.0% by weight of quince, 10 to 15% by weight of mint, 5 to 15% by weight of lemon, 10 to 17% by weight of green tea, 0.05 to 0.2% by weight of propolis, 0.1 to 0.3% by weight of monk fruit, 0.5 to 1.5% by weight of magnesium stearate and 0.5 to 1.5% by weight of silicon dioxide, based on the weight of the total composition.

Further, the present invention provides a method for suppressing oral malodor, comprising applying to oral cavity the above composition.

Further, the present invention provides a method of inhibiting growth of bacteria in oral cavity of a subject, comprising applying to the oral cavity the above composition.

Advantageous Effects

The ingestible tablet or powder type oral cleaning composition according to the present invention has an advantage of being easy to carry and use because it is provided in a tablet or powder form instead of a liquid or gel form. In addition, since the present composition does not contain chemical components but uses natural materials and thus can be ingested after use, it does not require a space where it can be spit out, and therefore, has a convenience of using it at any time regardless of the location. Furthermore, it exhibits excellent efficacy in inhibiting oral bacteria and removing bad breath, and has excellent taste palatability.

BRIEF DESCRIPTION OF DRAWINGS

FIG. 6B shows a harmful bacteria inhibition rate of Example 2 for 11 kinds of harmful bacteria.

DETAILED DESCRIPTION OF EMBODIMENTS

Figure 1:
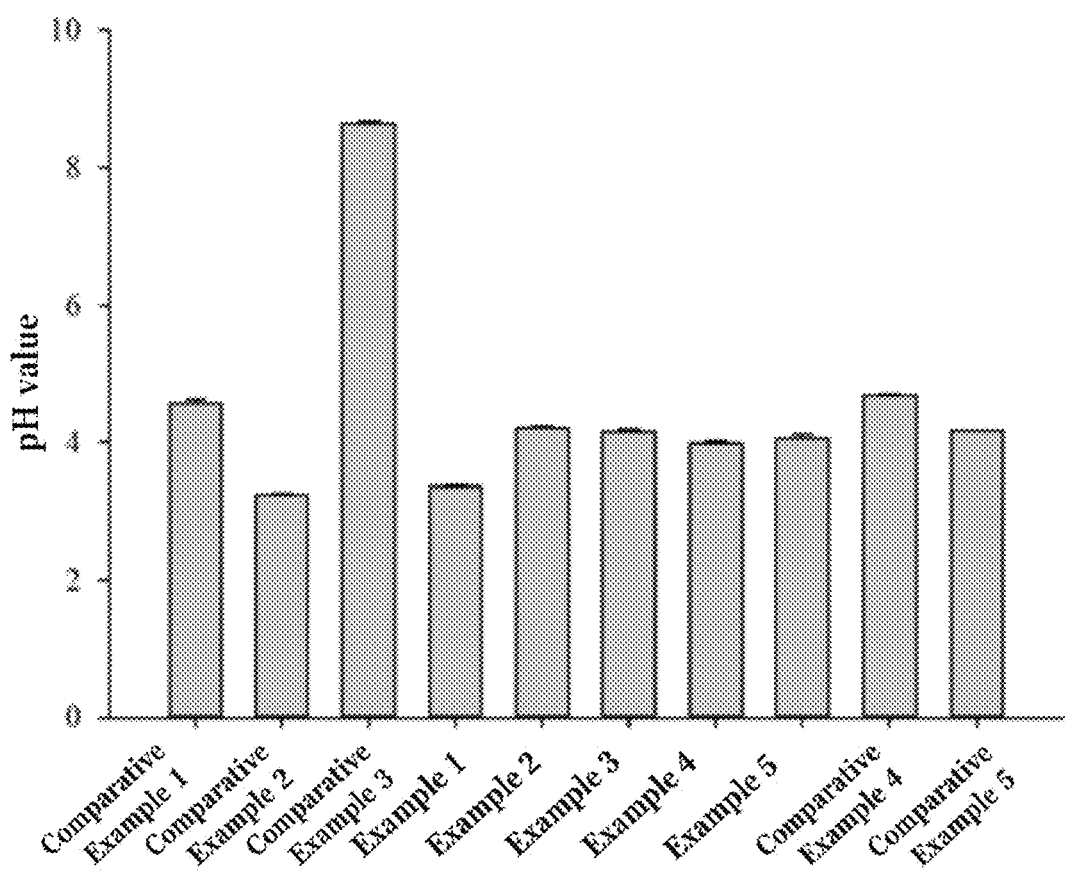
FIG. 1 shows pH measurement results of oral cleaning compositions of Examples and Comparative Examples.
Figure 2A:
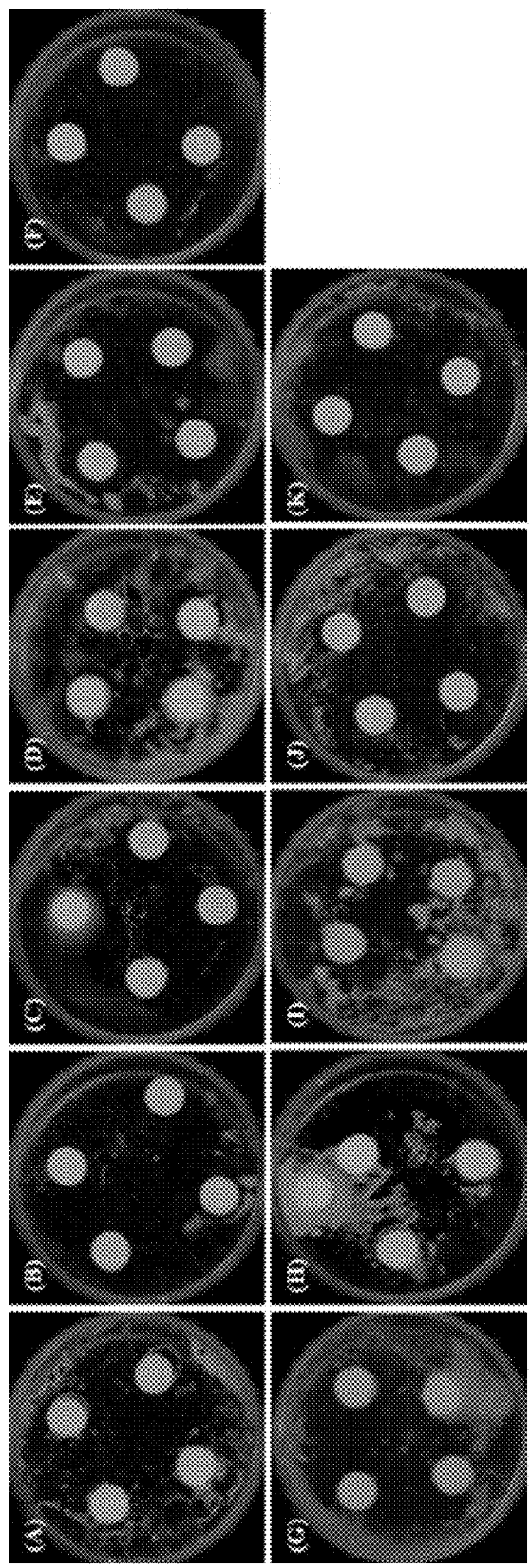
FIG. 2A is a photograph of a culture dish 24 hours after applying a sample of Comparative Example 1 to 11 kinds of harmful bacteria.
Figure 2B:
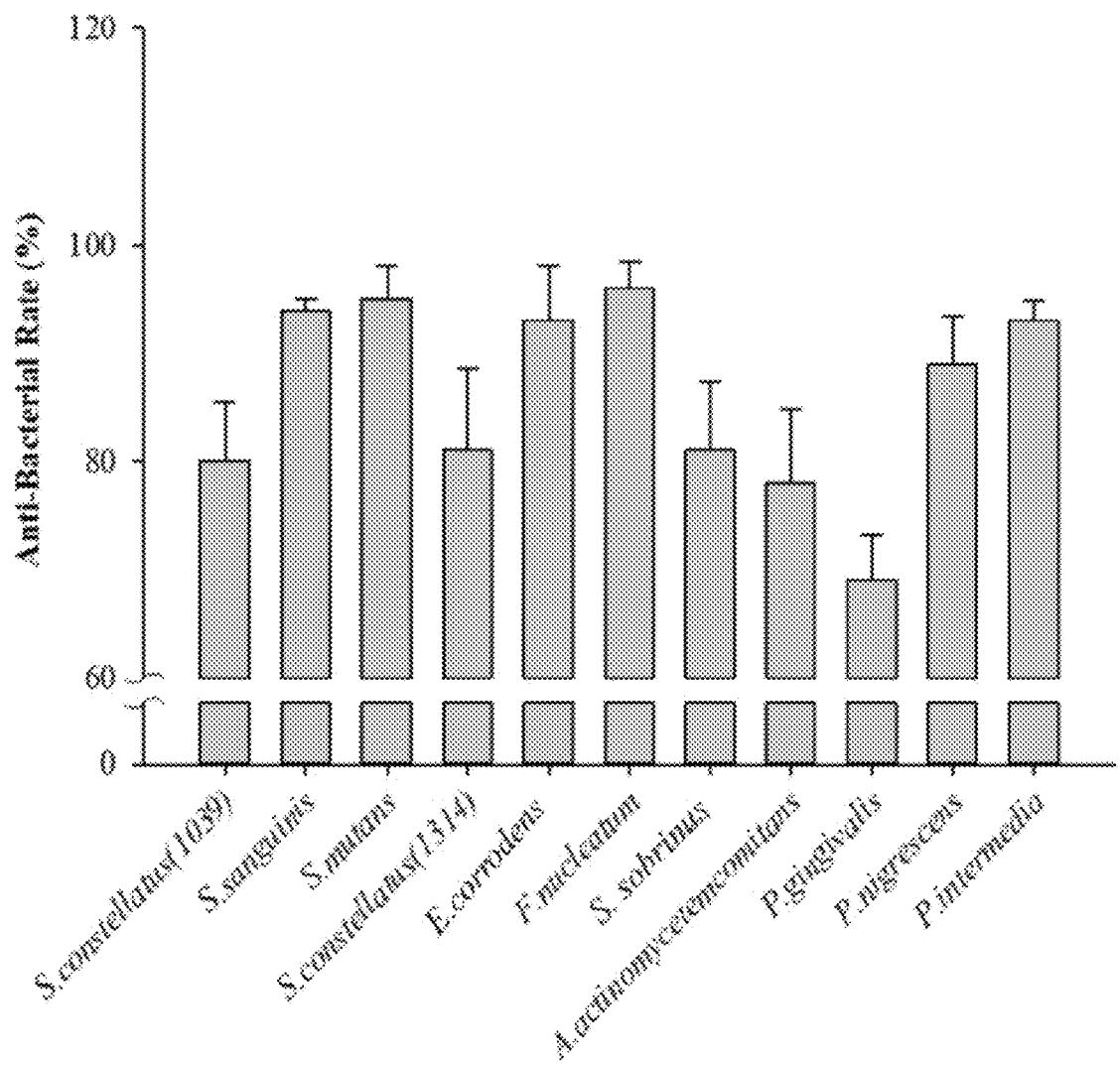
FIG. 2B shows a harmful bacteria inhibition rate of Comparative Example 1 for 11 kinds of harmful bacteria.
Figure 3A:
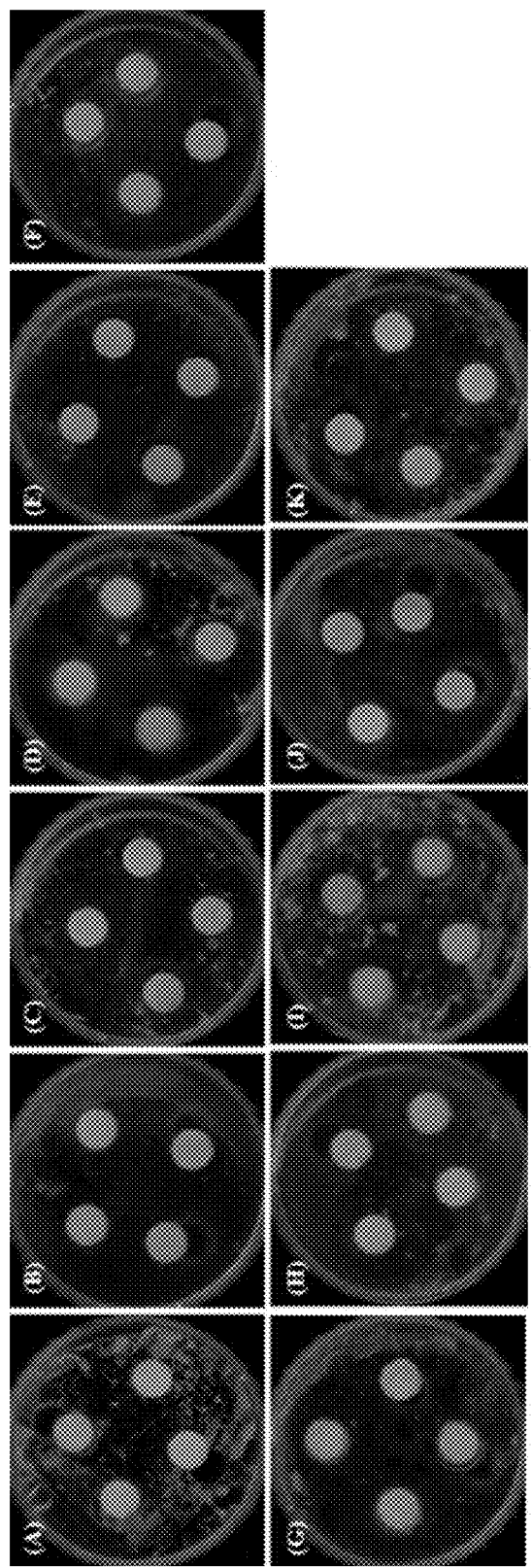
FIG. 3A is a photograph of a culture dish 24 hours after applying a sample of Comparative Example 2 to 11 kinds of harmful bacteria.
Figure 3B:
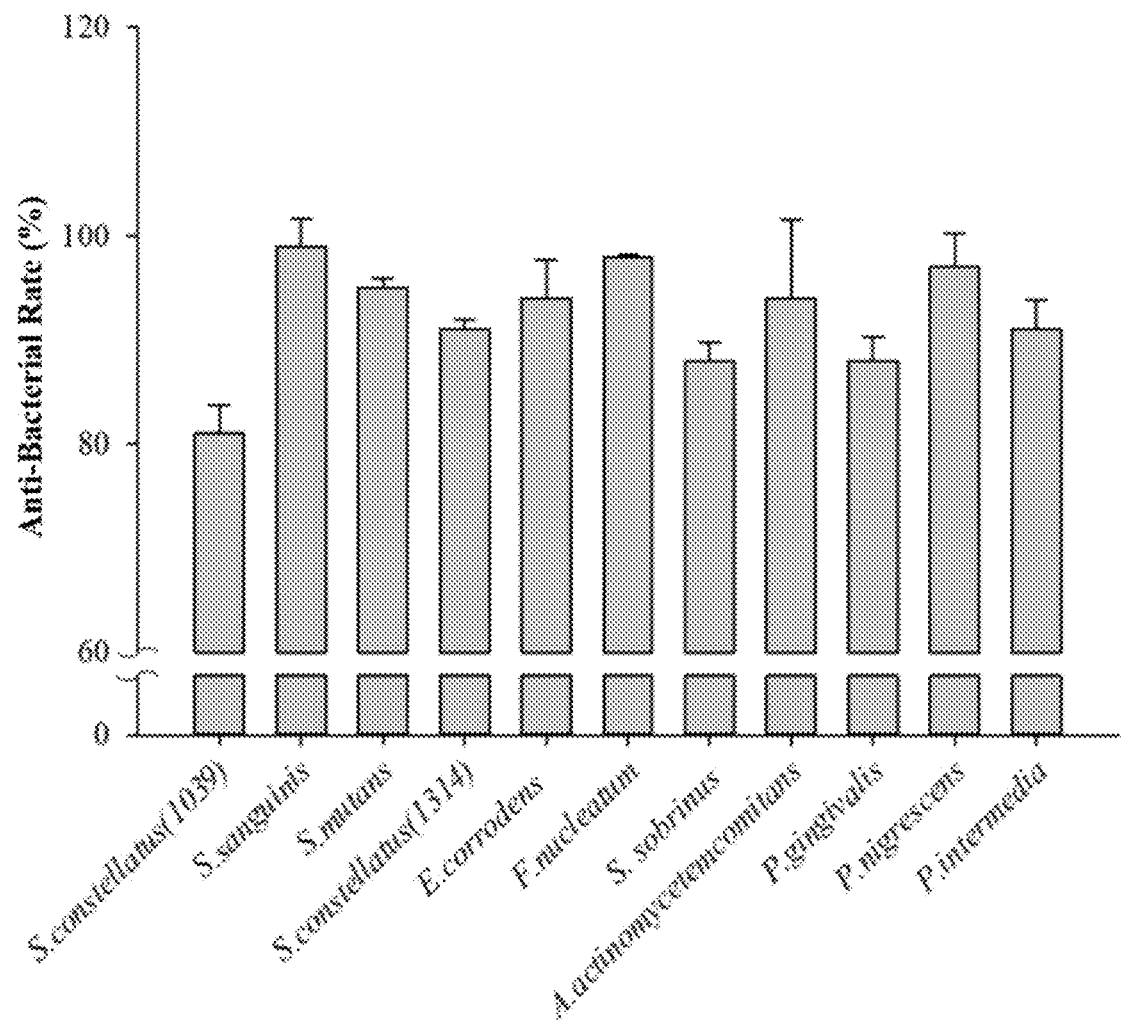
FIG. 3B shows a harmful bacteria inhibition rate of Comparative Example 2 for 11 kinds of harmful bacteria.
Figure 4A:
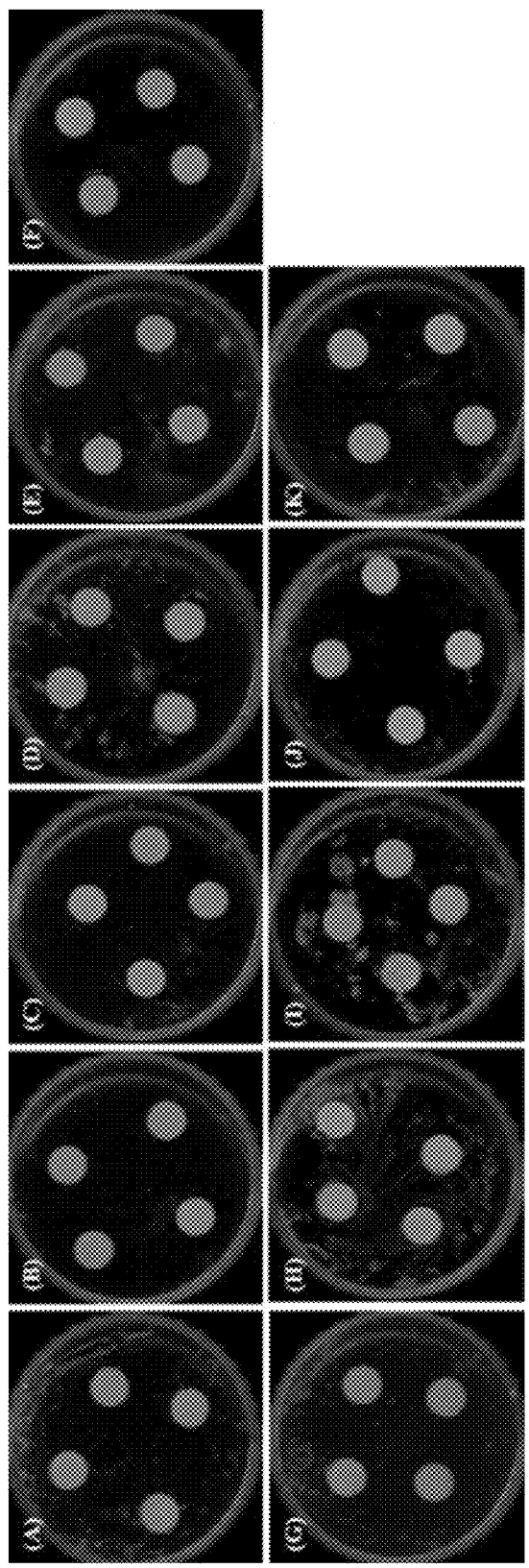
FIG. 4A is a photograph of a culture dish 24 hours after applying a sample of Comparative Example 3 to 11 kinds of harmful bacteria.
Figure 4B:
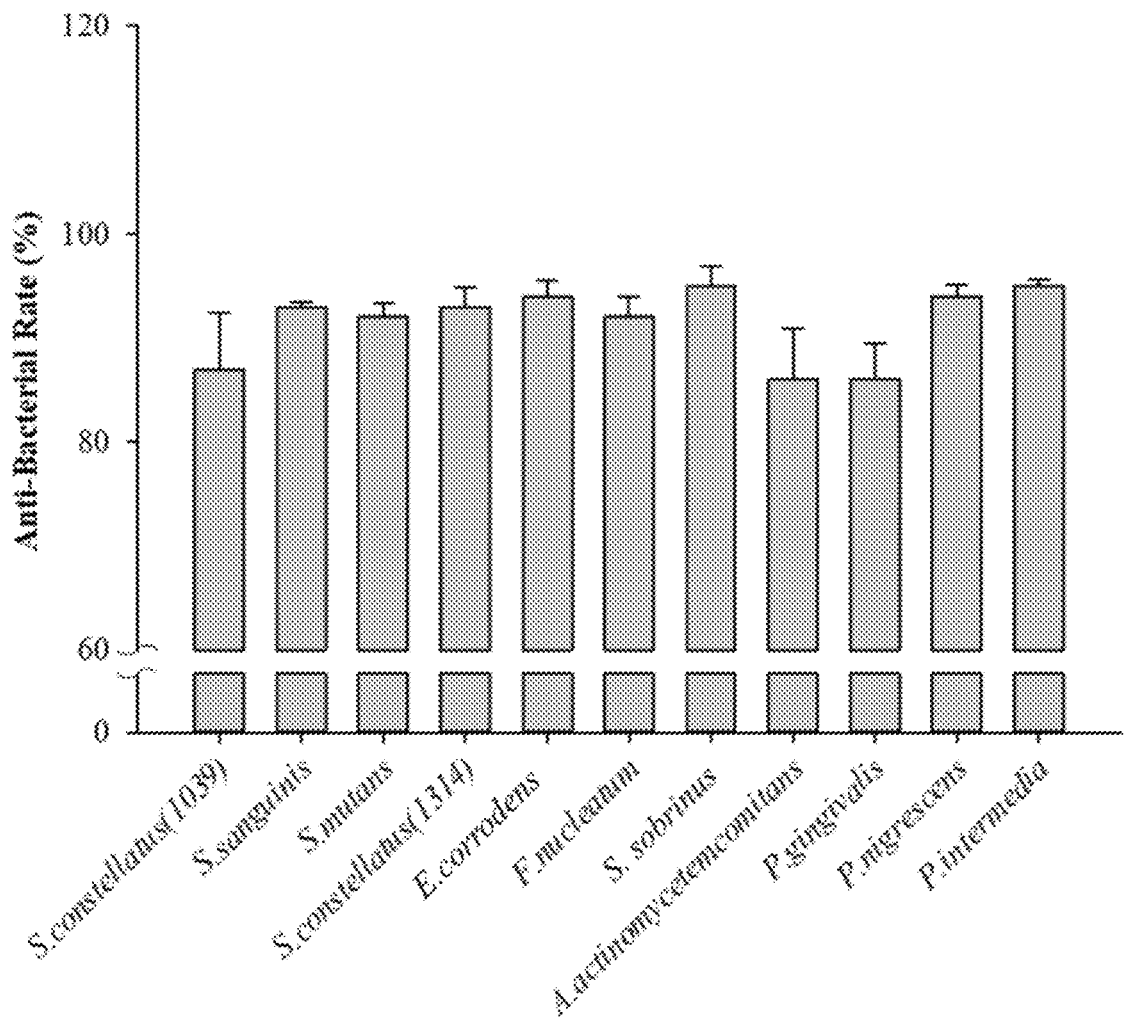
FIG. 4B shows a harmful bacteria inhibition rate of Comparative Example 3 for 11 kinds of harmful bacteria.
Figure 5A:
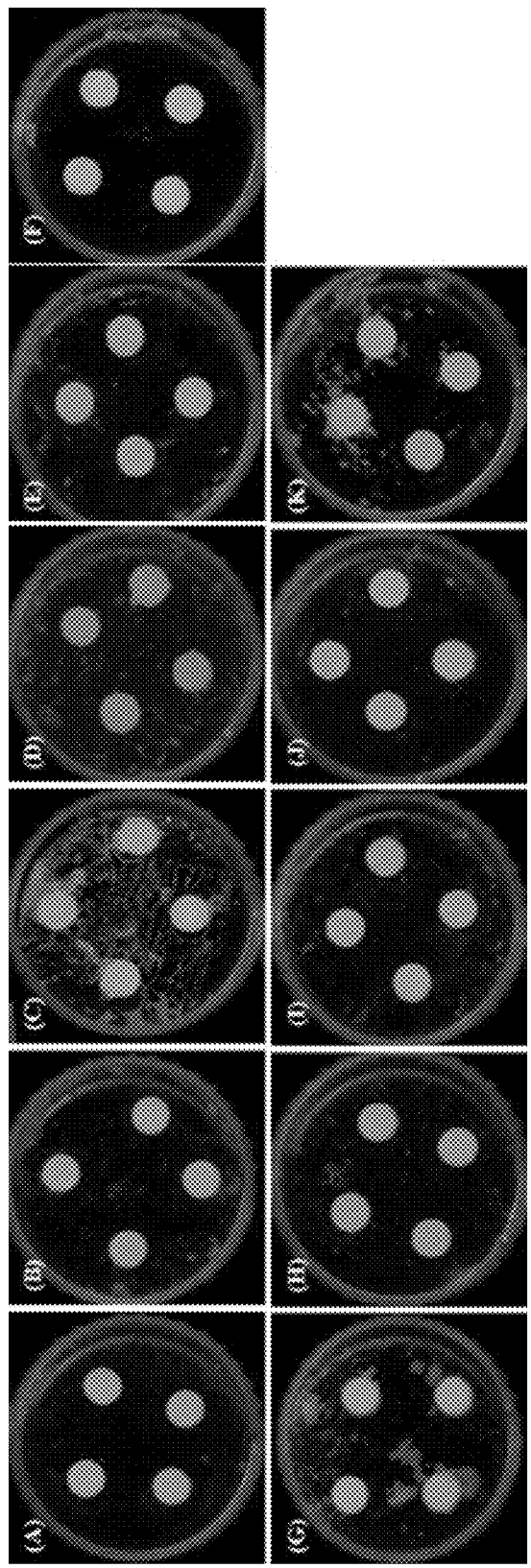
FIG. 5A is a photograph of a culture dish 24 hours after applying a sample of Example 1 to 11 kinds of harmful bacteria.
Figure 5B:
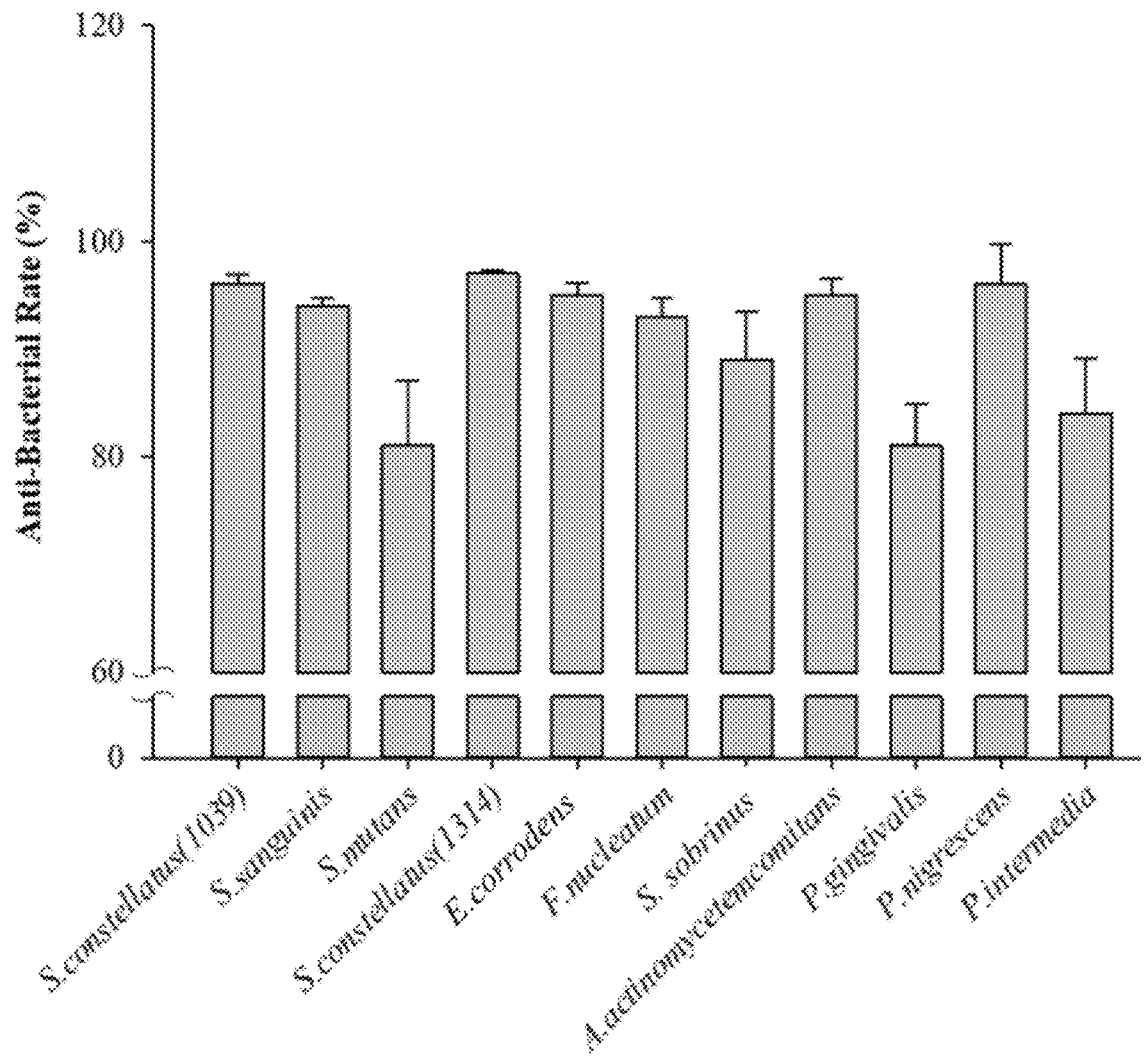
FIG. 5B shows a harmful bacteria inhibition rate of Example 1 for 11 kinds of harmful bacteria.
Figure 6A:
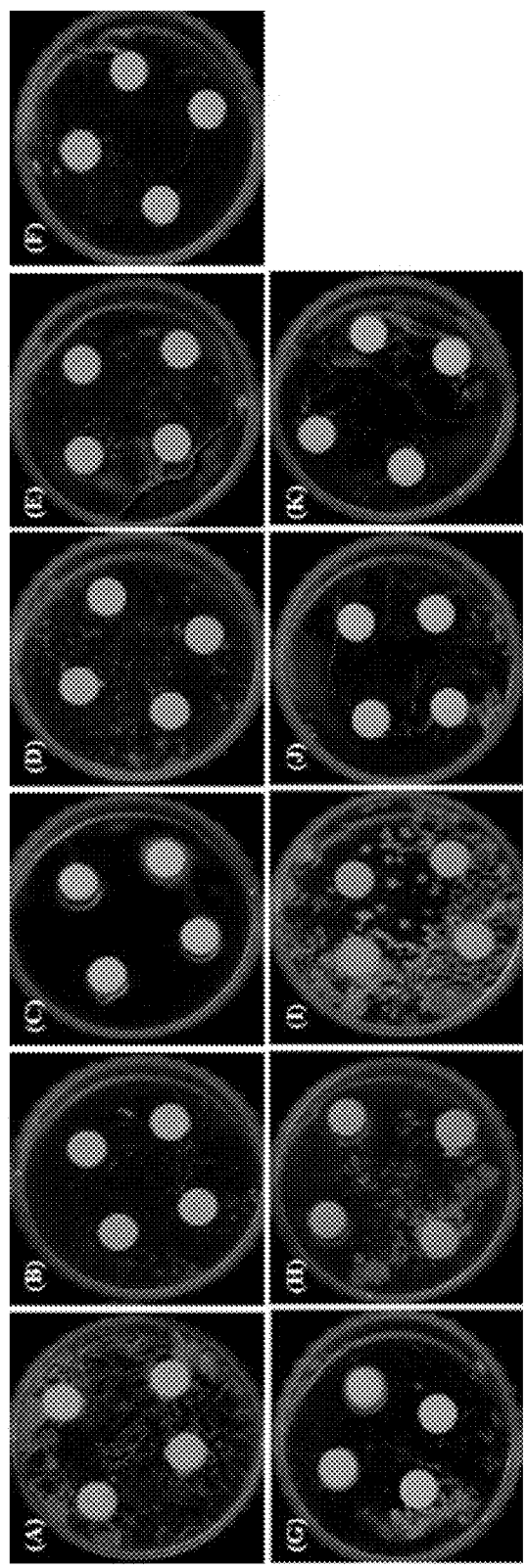
FIG. 6A is a photograph of a culture dish 24 hours after applying a sample of Example 2 to 11 kinds of harmful bacteria.
Figure 7A:
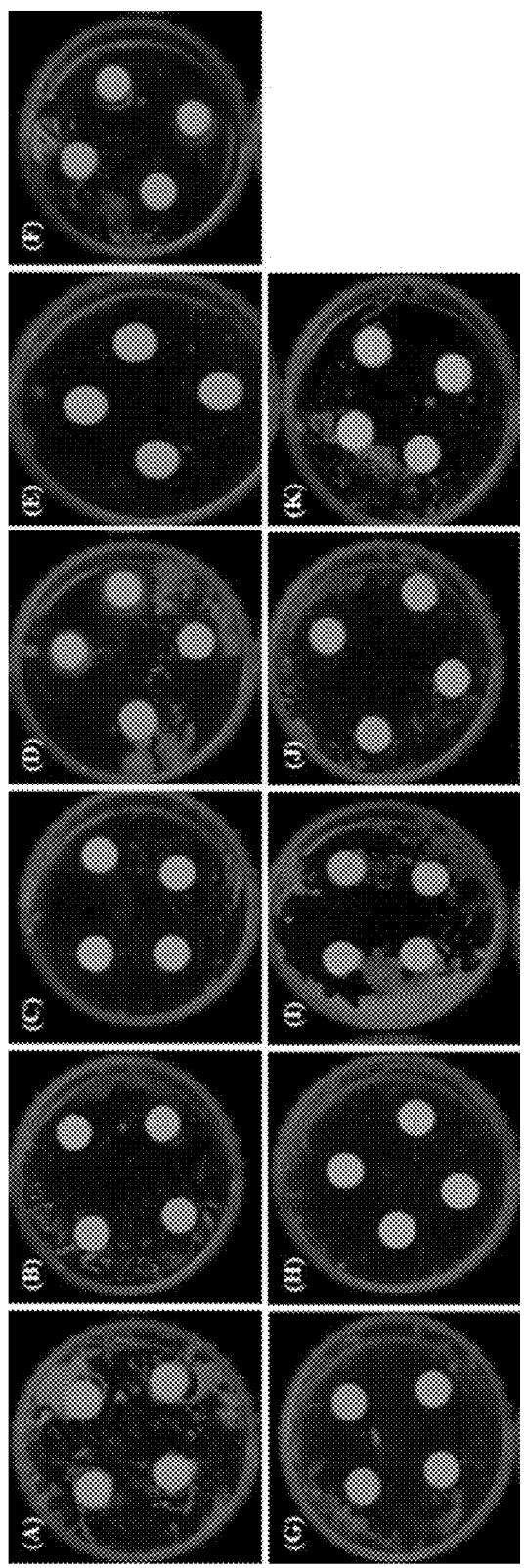
FIG. 7A is a photograph of a culture dish 24 hours after applying a sample of Example 3 to 11 kinds of harmful bacteria.
Figure 7B:
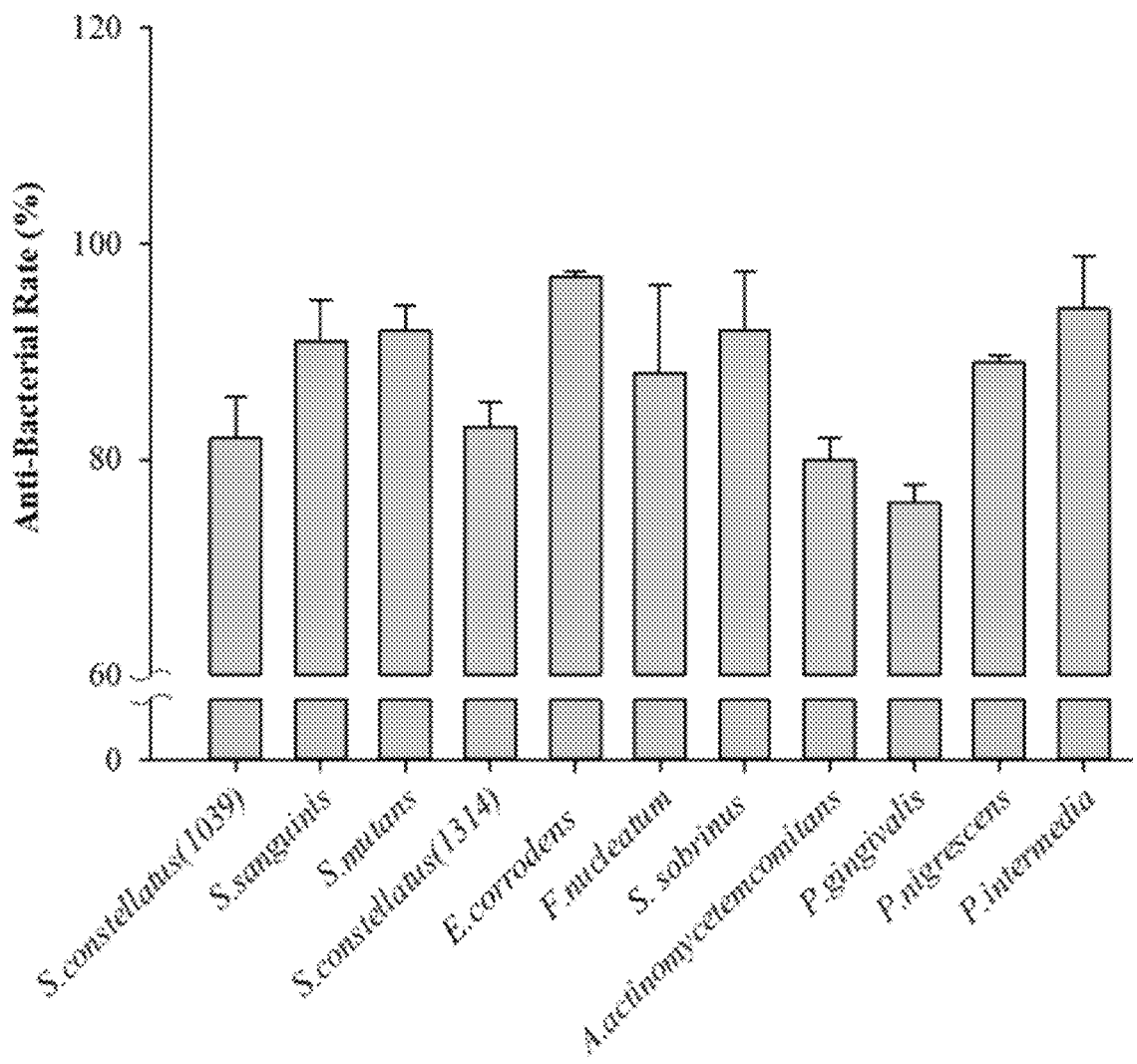
FIG. 7B shows a harmful bacteria inhibition rate of Example 3 for 11 kinds of harmful bacteria.
Figure 8A:
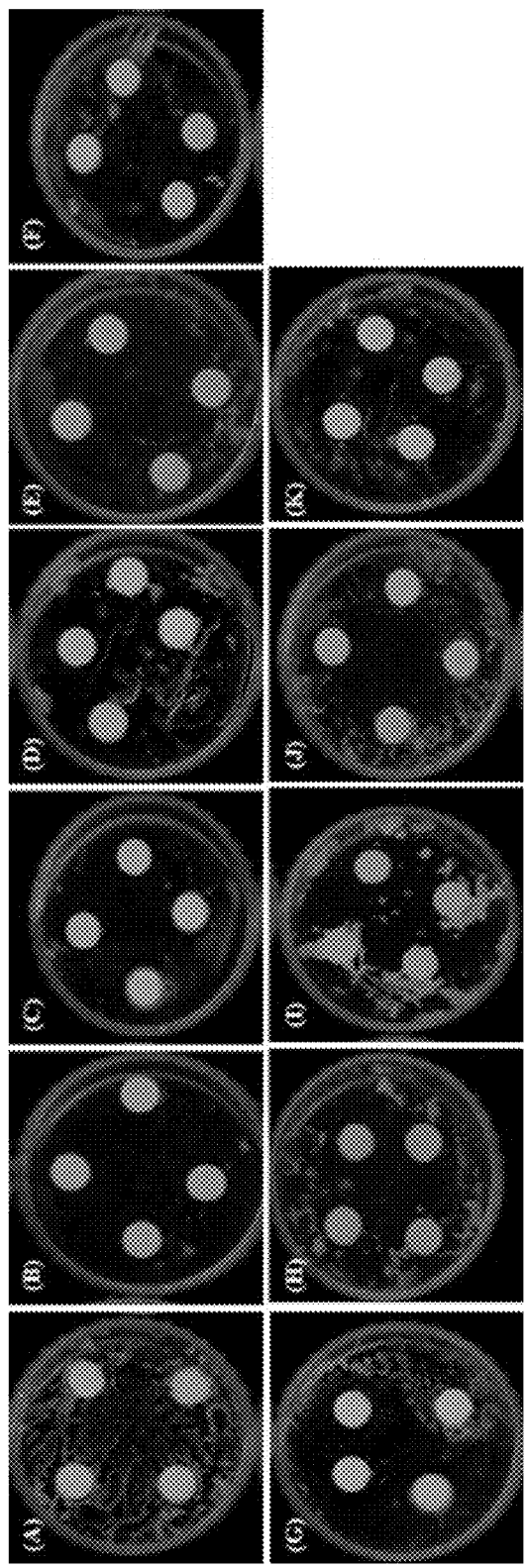
FIG. 8A is a photograph of a culture dish 24 hours after applying a sample of Example 4 to 11 kinds of harmful bacteria.
Figure 8B:
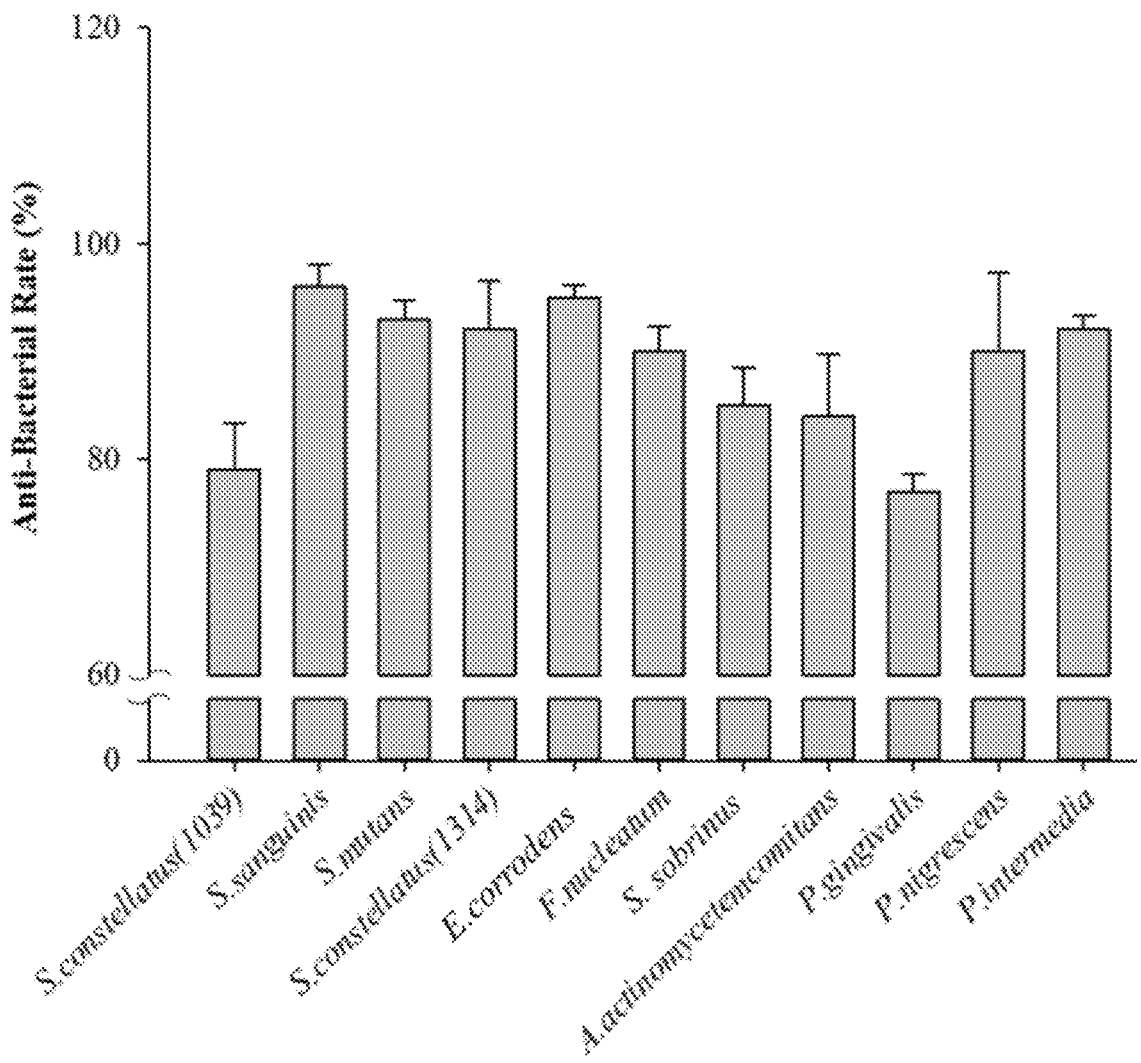
FIG. 8B shows a harmful bacteria inhibition rate of Example 4 for 11 kinds of harmful bacteria.
Figure 9A:
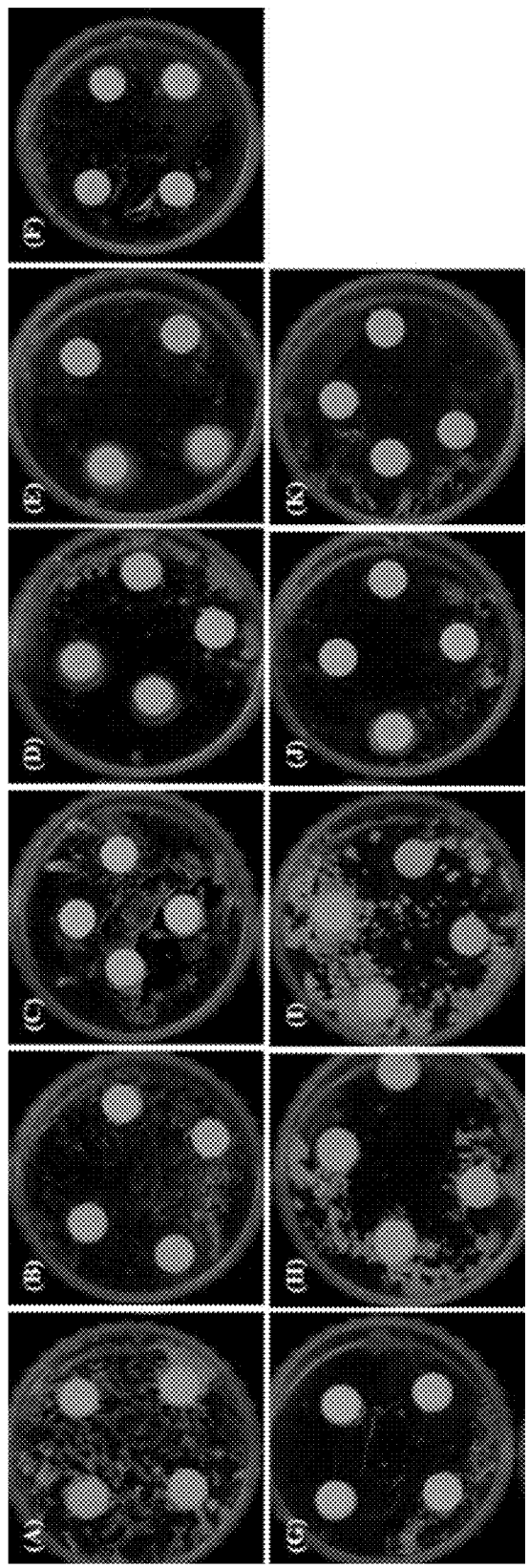
FIG. 9A is a photograph of a culture dish 24 hours after applying a sample of Example 5 to 11 kinds of harmful bacteria.
Figure 9B:
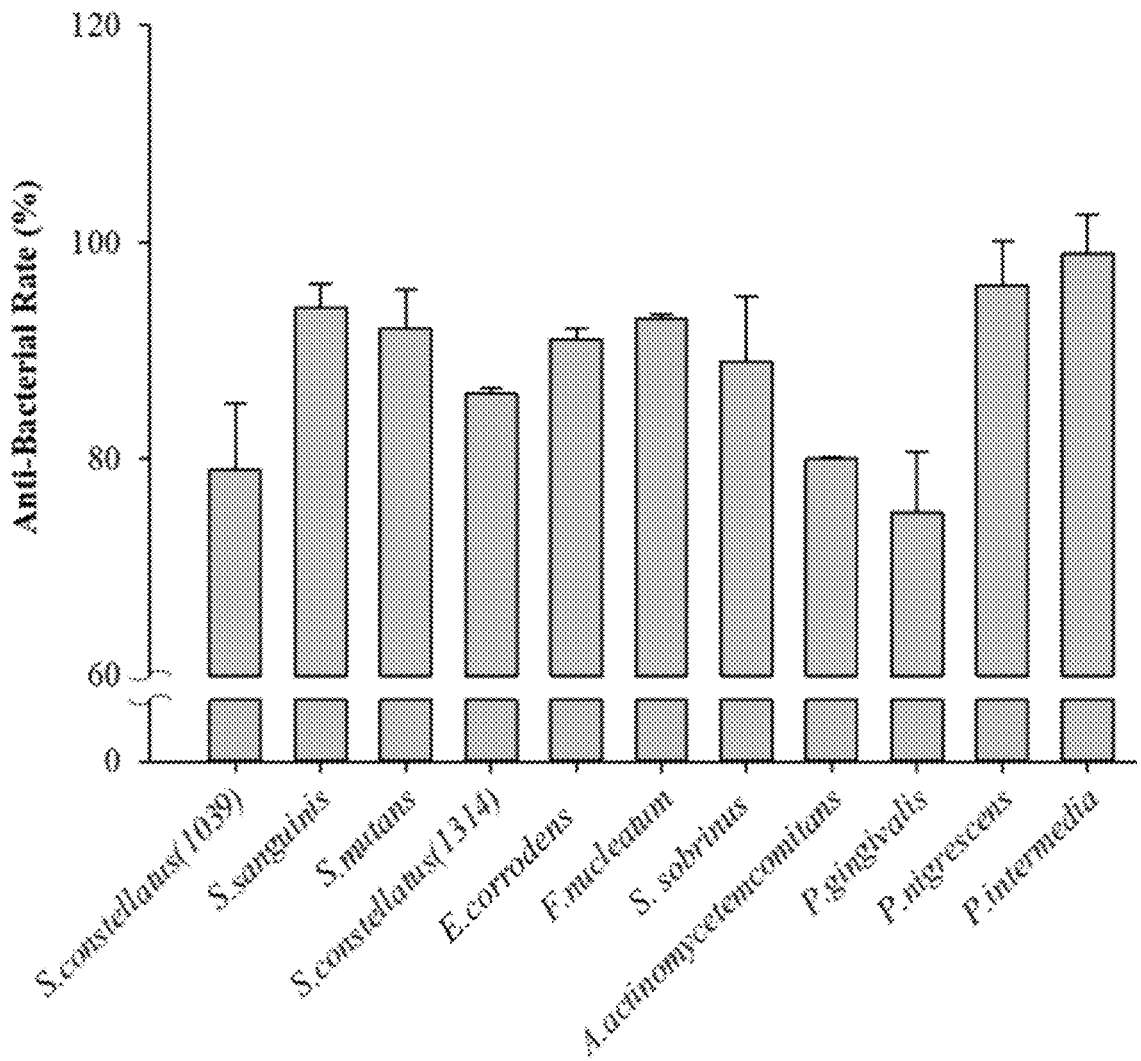
FIG. 9B shows a harmful bacteria inhibition rate of Example 5 for 11 kinds of harmful bacteria.
Figure 10A:
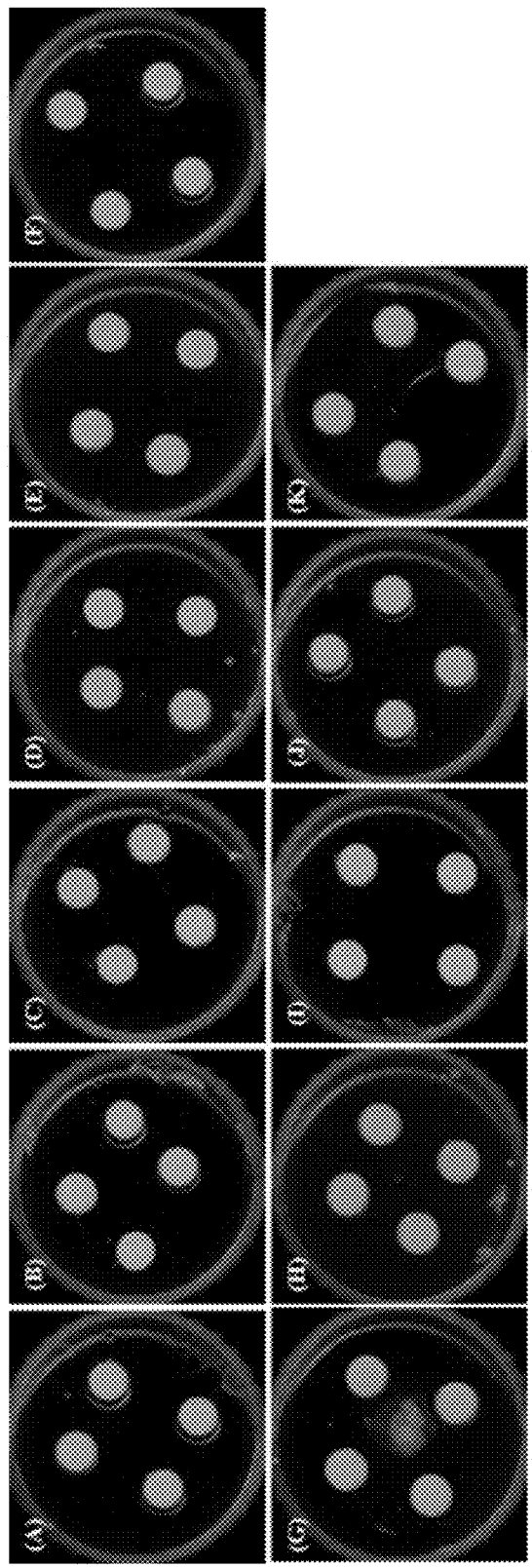
FIG. 10A is a photograph of a culture dish 24 hours after applying a sample of Comparative Example 4 to 11 kinds of harmful bacteria.
Figure 10B:
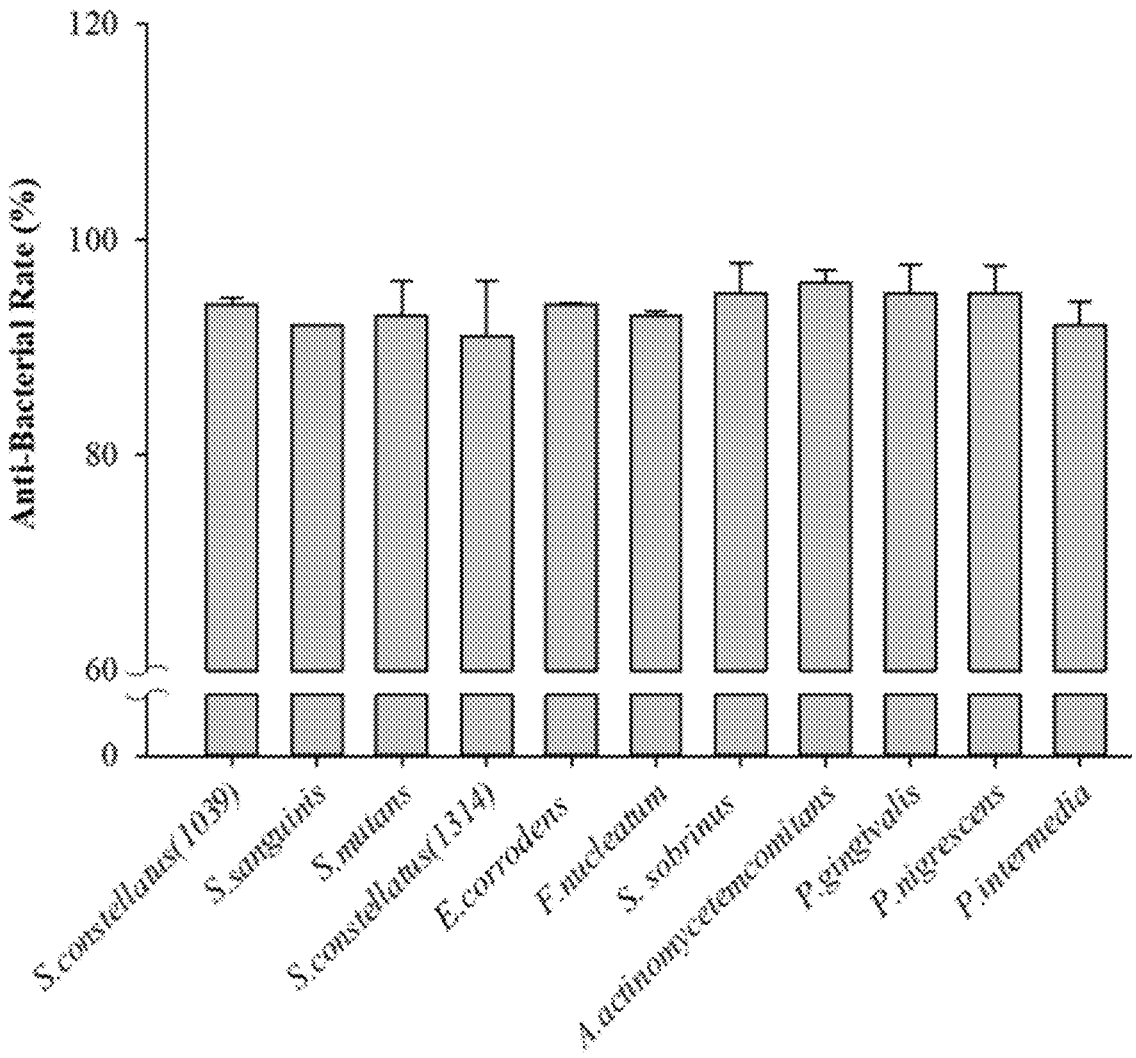
FIG. 10B shows a harmful bacteria inhibition rate of Comparative Example 4 for 11 kinds of harmful bacteria.
Figure 11A:
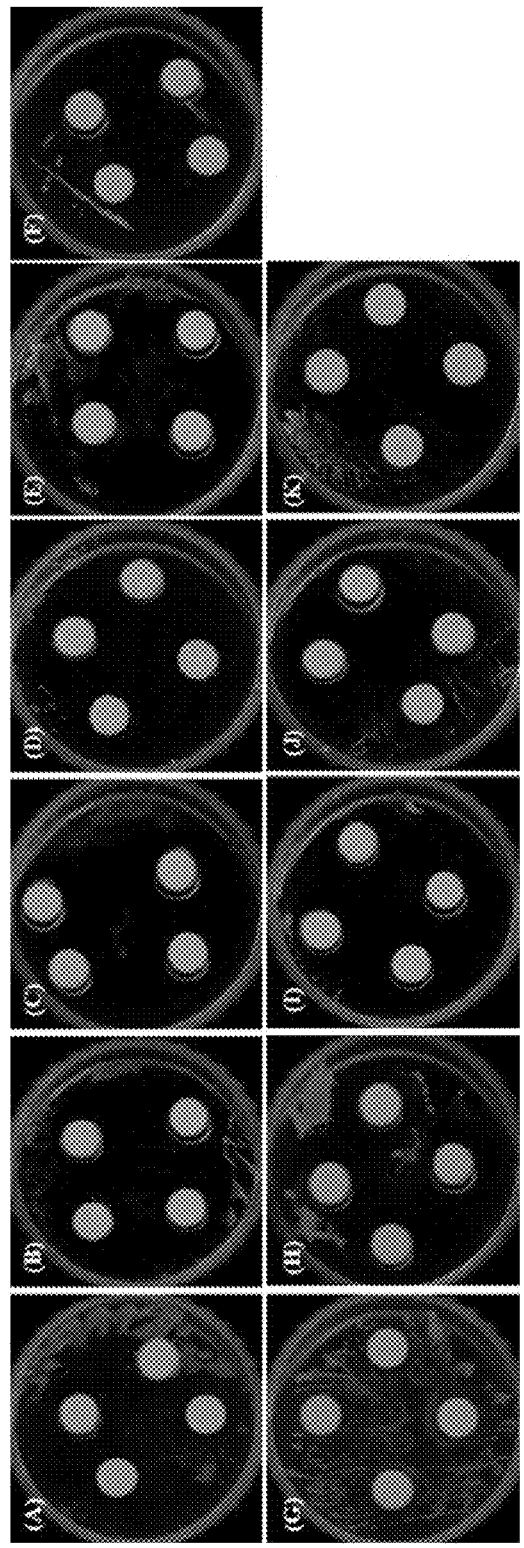
FIG. 11A is a photograph of a culture dish 24 hours after applying a sample of Comparative Example 5 to 11 kinds of harmful bacteria.
Figure 11B:
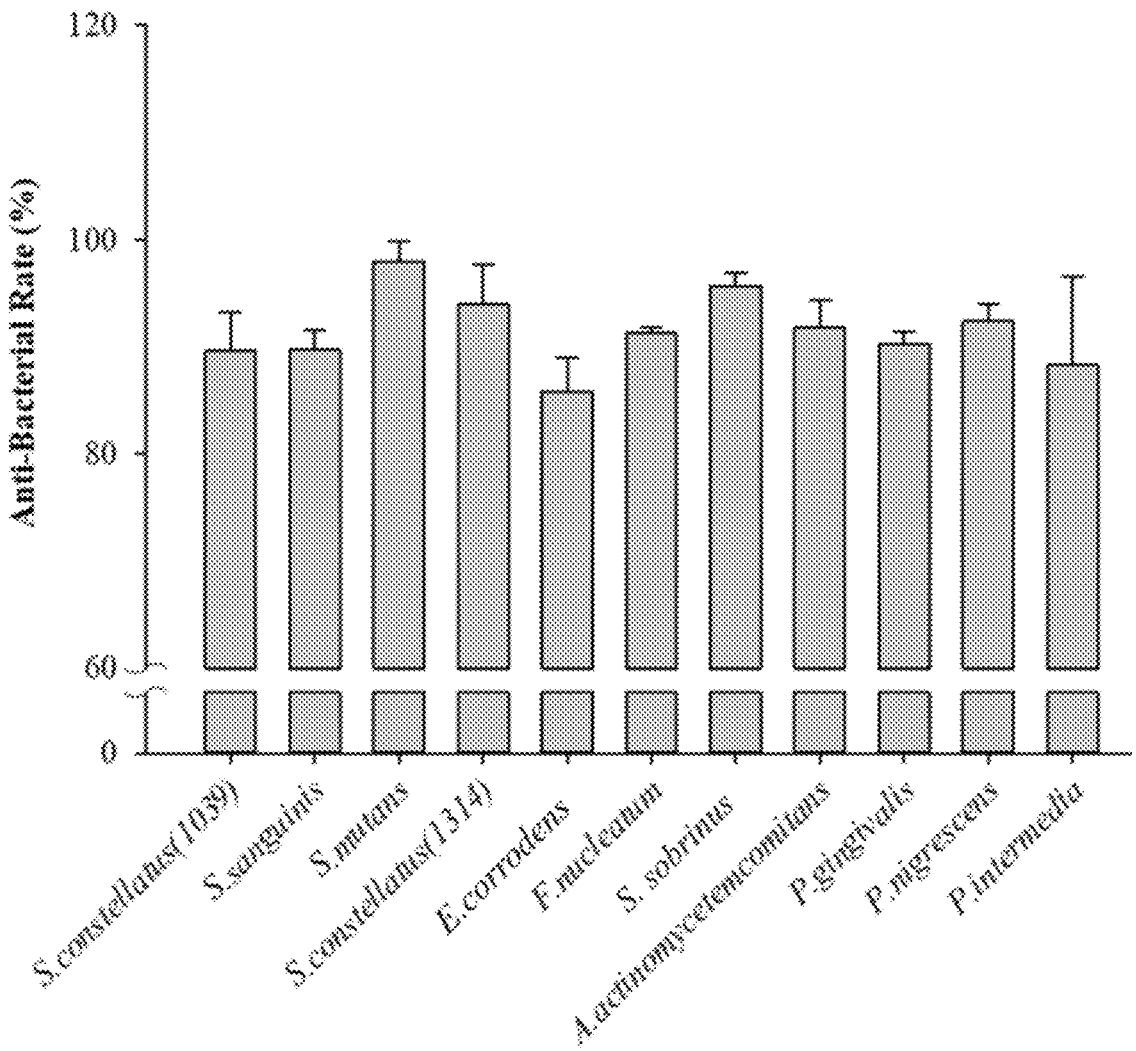
FIG. 11B shows a harmful bacteria inhibition rate of Comparative Example 5 for 11 types of harmful bacteria.
Figure 12A:
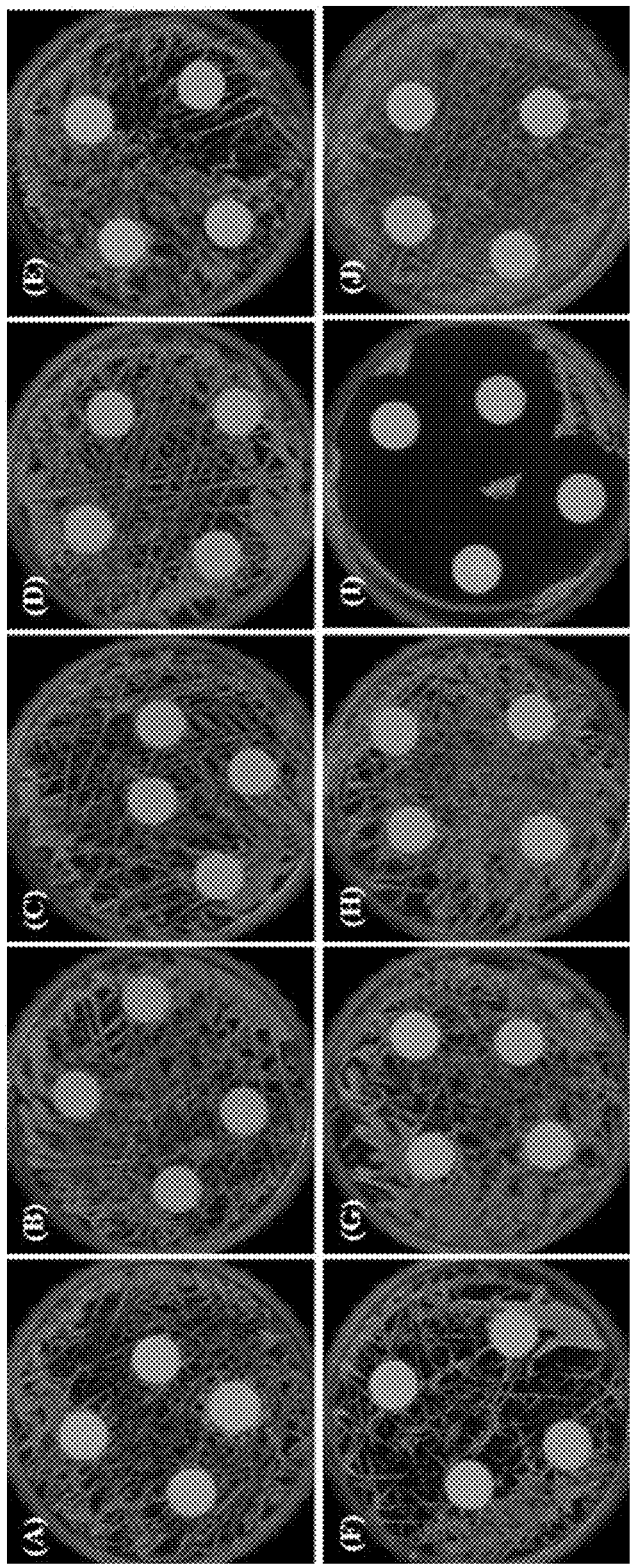
FIG. 12A is a photograph of a culture dish 24 hours after applying samples of Examples and Comparative Examples to *Streptococcus salivarius*.
Figure 12B:
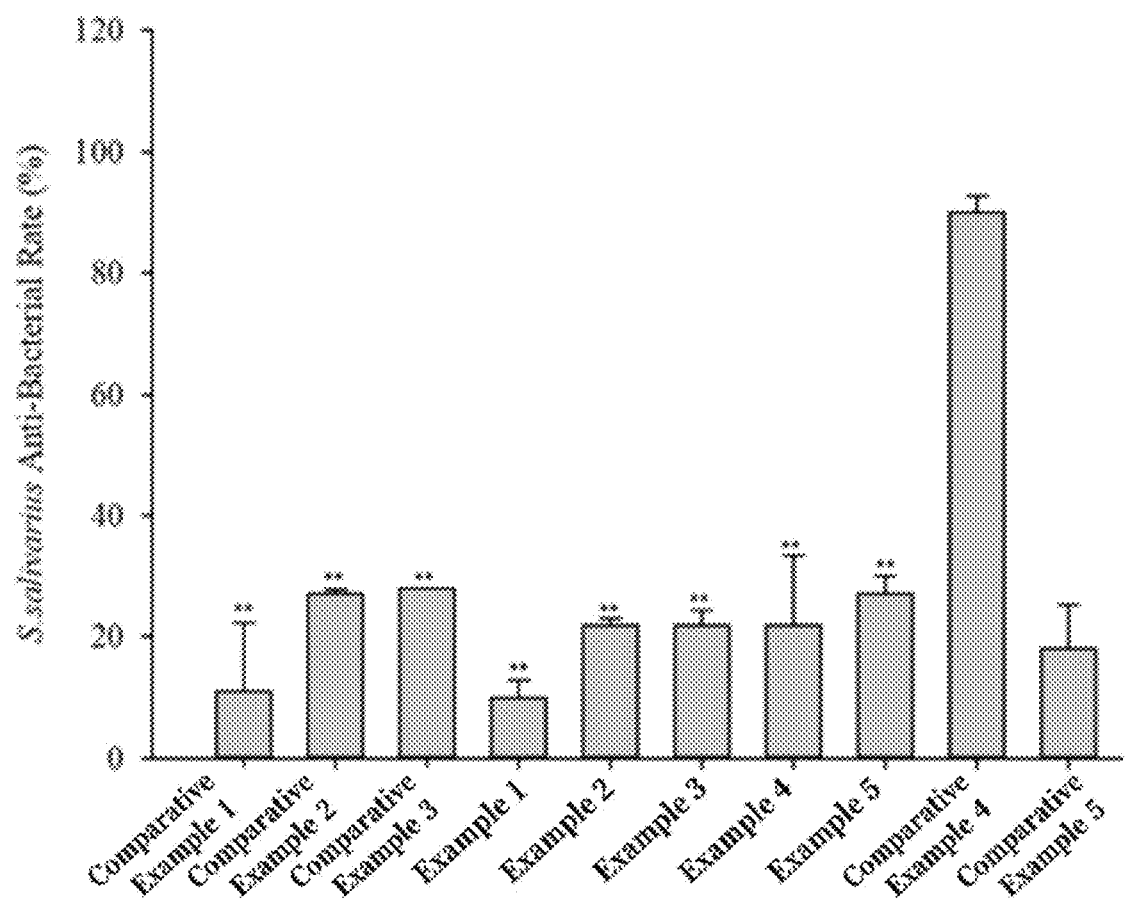
FIG. 12B shows an inhibition rate of samples of Examples and Comparative Examples for *Streptococcus salivarius*.
Figure 13A:
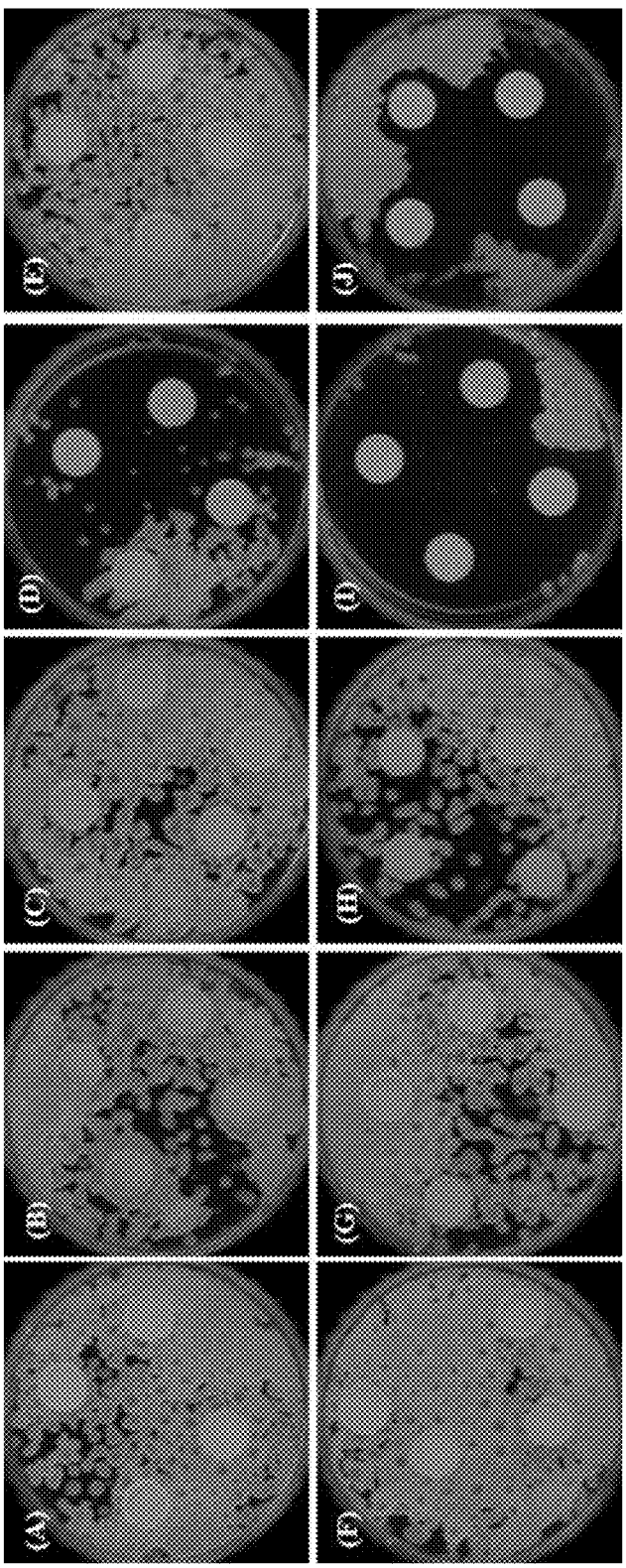
FIG. 13A is a photograph of a culture dish 24 hours after applying samples of Examples and Comparative Examples to *Lactobacillus salivarius*.
Figure 13B:
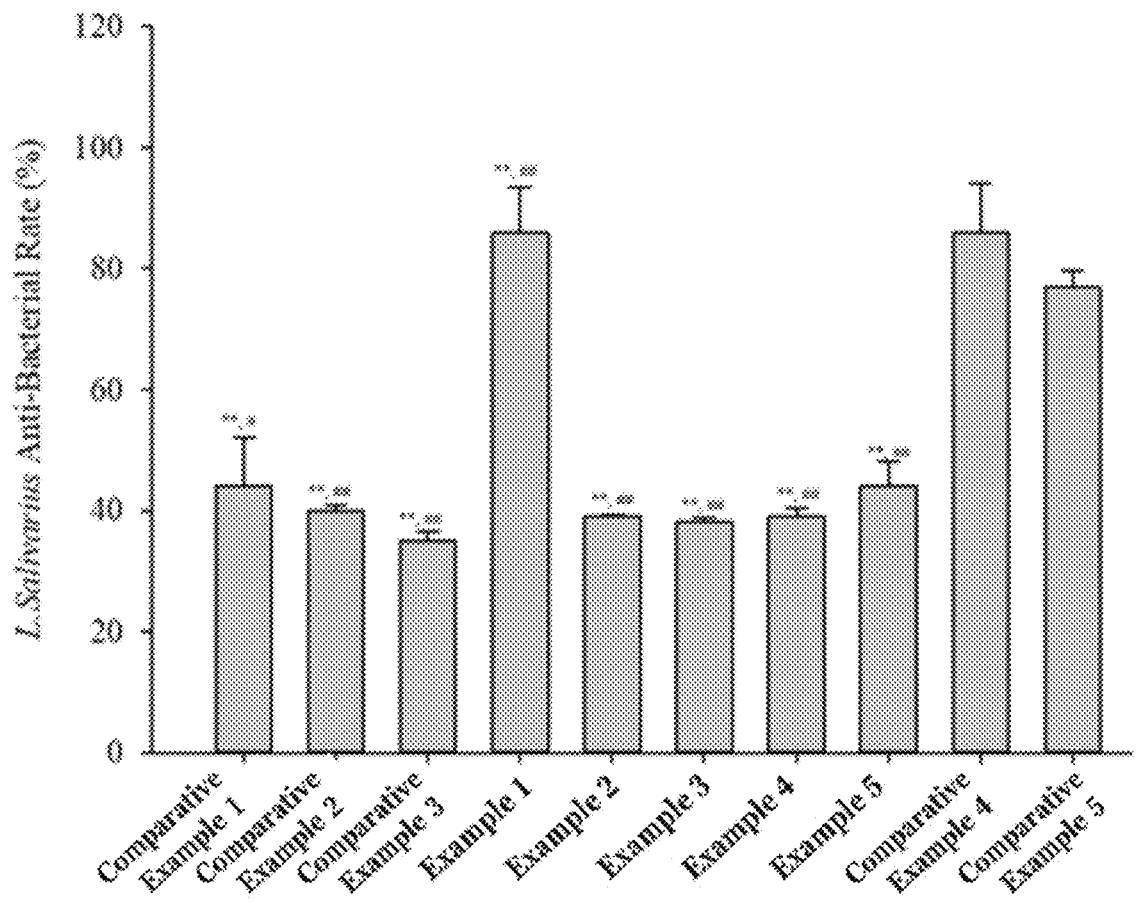
FIG. 13B shows an inhibition rate of samples of Examples and Comparative Examples for *Lactobacillus salivarius*.

Unless otherwise defined, all technical and scientific terms used in this specification have the same meaning as commonly understood by those skilled in the art to which the present invention belongs. In general, the nomenclature used in the specification is well known and commonly used in the art.

The present invention relates to a tablet or powder type oral cleaning composition, and more particularly a tablet or powder type oral cleaning composition for dental health, which includes salt, xylitol, bellflower, quince and mint in a specific compositional ratio and thus, has excellent anti-inflammatory and antibacterial effects and is effective in removing bad breath, and is composed of only natural ingredients and thus can be ingested.

The tablet or powder type oral cleaning composition according to the present invention may preferably comprise 3 to 10% by weight of salt, 40 to 70% by weight of xylitol, 0.5 to 15% by weight of bellflower, 0.1 to 15% by weight of quince, and 10 to 15% by weight of mint.

In the present invention, the salt is preferably a solar salt, and in particular, the solar salt is preferably an enzyme salt inoculated with enzyme using a fermented wild grass juice after washing, drying and sterilization.

Hereinafter, a method of preparing the enzyme salt will be described in detail.

A freshly collected solar salt includes a large amount of water, bittern, and impurities. In order to remove these, the solar salt may be washed with fresh water, dehydrated, and then dried and sterilized to remove the water, bittern and impurities. In this case, the drying and sterilization may be performed for 30 to 60 minutes using a microwave, and is preferably performed at 120 to 150° C.

The salt dried and sterilized by the above process can be enzymatically inoculated by spraying the fermented wild grass juice at 36 to 40° C.

The fermented wild grass juice may be prepared by using 10 or more, preferably 20 kinds of medicinal herbs selected from the group consisting of Injin Mugwort, Eoseongcho, Black Garlic, Silkworm, Seokchangpo, Indongcho, *Aralia* root, Gasiogapi, Sambaekcho, Mistletoe, Galgeun, Pork Potato, Pine Needle, *Angelica, Ganoderma lucidum* Mushroom, *Cornus*, Goji, Licorice, Jujube, Hasuo, Baekbokryeong, Heatgae Fruit, Tobokryeong, mulberry leaves, yugeunpi, cinnamon, nasturtium, fermented camphor *ginseng*, thistle, tea fern, purslane and jepi in a certain ratio.

The fermented wild grass juice is obtained by collecting and washing medicinal herbs, and fermenting and aging them using sugar. The fermenting and aging processes are for extracting nutrients contained in raw materials without destroying them by storing the raw materials together with a sugar solution for a long time and fermenting and aging them by microorganisms, and sugar is basically used as the sugar solution. In the present invention, in order to make a health-oriented product, sugar and oligosaccharide are mixed and used as the sugar solution.

In one embodiment of the present invention, the fermented wild grass juice may be prepared by blending 10 to 40 parts by weight of sugar and 60 to 90 parts by weight of oligosaccharide, based on 100 parts by weight of medicinal herbs.

The sugar solution added in the above mixing ratio has advantages in that it is easy to control various bacteria at the beginning of fermentation and swells quickly compared to the case of using sugar alone. When the sugar is used alone, water contained in raw herbs is transferred to sugar through osmotic pressure at the beginning of fermentation, resulting in swelling, and at this time, as a concentration of the sugar solution increases, various bacteria remaining on the surface of the raw herbs are reduced by the osmotic pressure; however, there is a disadvantage that the manufacturing time is lengthened. However, in case where an appropriate oligosaccharide sugar solution is used, an initial swelling is faster than in the case of using sugar alone, and thus, the manufacturing time can be shortened by about a week.

The fermentation of the herb may be carried out for 20 to 60 days at a temperature of 10 to 20° C. If the fermentation proceeds for too long, alcohol is produced, and at a temperature above 20° C., the growth of acetic acid bacteria becomes active and thus, there is a possibility that a large amount of acetic acid may be produced. If it is less than the above range, the fermentation may not proceed well, or mold may grow.

The fermented herbal juice after the above fermentation is completed is separated into fiber and liquid, and the remaining fine fibers are thoroughly filtered using a micro filter, and then only the liquid is put in a jar to be aged. The aging may be carried out for 3 years or more at a temperature of 10 to 20° C., and when the aging period is less than 3 years, there is a problem that the taste and aroma of the herb are not sufficiently leached into an undiluted solution.

The fermented and aged herbal juice after the aging is completed is used after removing alcohol through distillation under reduced pressure to reduce the alcohol content to 1% or less, which is suitable for the Food Standard Act.

The alcohol-reduced herbal fermented juice is first sterilized in a high-temperature sterilizer. The first sterilization step may be carried out at a temperature of 85 to 100° C. for 30 to 50 minutes, and in the above range, bacterial growth can be effectively inhibited without destroying useful ingredients while not damaging the flavor such as the taste and aroma of the herbs. The first sterilized herbal fermented juice is hot-filled in a container and then cooled.

The hot-filling and cooling steps are processes in which the fermented juice is raised to a high temperature, filled and then rapidly cooled; and have the effects of inhibiting a damage to the herbal flavor due to a latent heat of a preheating liquid and increasing an efficiency of secondary sterilization by giving a thermal shock to the microorganism. Specifically, the hot-filling is carried out at a temperature of 85 to 95° C., and the cooling can lower the temperature to a temperature of 30 to 40° C., and there is an effect of improving the flavor of the herb and inhibiting the growth of bacteria at the temperature of the above range.

The cooled herbal fermented juice is secondarily sterilized in an ultra-high temperature instant sterilizer. The ultra-high temperature sterilization (UHT) may be carried out at a temperature of 100 to 140° C. for 2 to 40 seconds, and can remove heat-resistant spore-producing bacteria and various bacteria which have not been completely killed by the first sterilization.

The enzyme culture fluid produced as described above is concentrated to a concentration of 50 to 65 brix, and then mixed with sterilized water and a cultured bacteria mixture.

The cultured bacteria mixture includes enzymes such as protease, lipase, amylase, cellulase, SOD, etc. by beneficial bacteria such as *Lactobacillus bulgaricus, Lactobacillus acidophilus, Lactobacillus cassii, Lactobacillus plantarum, Streptcoccus thermophiles*, etc.

The herbal fermented juice may be cultured and fermented at a temperature of 35 to 37° C. for 48 to 72 hours in a culture tank and then used for enzyme inoculation.

The herbal fermented juice may be sprayed onto sterilized and dried salts to finally prepare enzyme salt.

The enzyme salt prepared by the above method has a characteristic that the bitter taste of itself is removed so that the heavy and salty taste is lightened.

The enzyme salt may be used as it is, or may be used after being liquefied at a temperature of 80 to 90° C. and then drying and powdering the liquefied material.

The enzyme salt of the present invention is effective in antioxidant, anti-cancer, immunity strengthening, aging prevention, and metabolic activity.

In the present invention, the salt is preferably comprised in an amount of 3 to 10% by weight, more preferably 4 to 7% by weight, and most preferably 4.5 to 5.0% by weight, based on the weight of the total composition.

The composition of the present invention may also comprise xylitol in an amount of 40 to 70% by weight, more preferably 45 to 60% by weight, and most preferably 55 to 60% by weight, based on the weight of the total composition.

Xylitol is a natural sweetener which is mainly used for toothpaste, gum, etc., and is known to be effective in improving bone mineral density and infecting influenza A, as well as preventing caries, as it does not form an acid which causes caries when used at 10 to 25 g per day.

The composition of the present invention may also comprise 0.1 to 15% by weight, more preferably 0.5 to 2.0% by weight, and most preferably 0.7 to 1.3% by weight of bellflowers, based on the total weight of the composition.

The bellflower is known to have anti-inflammatory, anti-allergic, anti-obesity, hyperlipidemia prevention, antibacterial, and antioxidant functions because it includes a large amount of physiologically active substances such as platycodin A, C, D and polygalacin D.

The bellflower may be used as a crushed and dried raw material, but it is preferable to use an extract in a powder form because there is a risk of being damaged during the manufacturing and distribution process.

According to an embodiment of the present invention, when the oral cleaning composition is prepared in a tablet form, the bellflower is preferably used in an amount of 0.5 to 2.0% by weight, more preferably 0.7 to 1.3% by weight.

According to another embodiment of the present invention, when the oral cleaning composition is prepared in a powder form, the bellflower is preferably used in an amount of 5 to 15% by weight, and more preferably 8 to 12% by weight.

The composition of the present invention may also comprise 0.1 to 15% by weight, more preferably 0.2 to 2.0% by weight, and most preferably 0.3 to 0.7% by weight of quince, based on the total weight of the composition.

It has been known from ancient times that the quince can prevent colds and relieve symptoms, and the quince contains vitamins, tannins, pectin, citric acid, potassium, polyphenol, etc., and thus, is active in antiviral, anti-inflammatory, antioxidant, delayed glucose absorption and dementia treatment.

The quince may be used as a crushed and dried raw material, but it is preferable to use an extract in a powder form because there is a risk of being damaged during the manufacturing and distribution process.

According to an embodiment of the present invention, when the oral cleaning composition is prepared in a tablet form, the quince is preferably used in an amount of 0.2 to 2.0% by weight, and more preferably 0.3 to 0.7% by weight.

According to another embodiment of the present invention, when the oral cleaning composition is prepared in a powder form, the quince is preferably used in an amount of 5 to 15% by weight, and more preferably 8 to 12% by weight.

The composition of the present invention may also comprise 5 to 20% by weight, more preferably 10 to 15% by weight, and most preferably 13 to 14% by weight of mint, based on the weight of the total composition.

The mint has been known to have antioxidant and tissue damage prevention effects as it is rich in phenolic and flavonoid components.

According to an embodiment of the present invention, when the oral cleaning composition is prepared in a tablet form, the mint is preferably used in an amount of 10 to 15% by weight, and more preferably 13 to 14% by weight.

According to another embodiment of the present invention, when the oral cleaning composition is prepared in a powder form, the mint is preferably 10 to 12% by weight.

In the present invention, the mint may be used in the form of an extract or an extract powder.

The present invention may further include ingredients having anti-inflammatory and antibacterial effects such as lemon, green tea, propolis and monk fruit.

The lemon is known to be rich in flavonoids, ascorbic acid and minerals, etc. and thus to have anti-aging, bactericidal, anti-inflammatory and antiviral effects, and has a lipid-lowering effect.

The lemon is preferably used in the form of a lemon extract or a powder of the extract.

The lemon may be comprised in 1 to 20% by weight based on the weight of the total composition. According to an embodiment of the present invention, when the oral cleaning composition is prepared in a tablet form, the lemon is preferably comprised in 5 to 15% by weight, more preferably 8 to 10% by weight. According to another embodiment of the present invention, when the oral cleaning composition is prepared in a powder form, the lemon is preferably 3 to 7% by weight.

The green tea contains a catechin and thus, helps in antioxidant, reducing body fat and improving blood cholesterol; and studies on its antibacterial efficacy have also been reported.

The green tea is preferably used in the form of a green tea extract or a powder of the extract.

In the present invention, the green tea may be comprised in 5 to 20% by weight based on the weight of the total composition. According to an embodiment of the present invention, when the oral cleaning composition is prepared in a tablet form, the green tea is preferably comprised in 10 to 17% by weight, more preferably 11 to 13% by weight. According to another embodiment of the present invention, when the oral cleaning composition is prepared in a powder form, the green tea is preferably 5 to 10% by weight.

The propolis refers to a substance made by mixing a tree secretion collected by bees with the bees' saliva and beeswax, and has long been used as a folk medicine. The propolis is known to include a variety of active ingredients such as flavonoids and polyphenols and thus to be excellent in anti-inflammatory, anti-viral, anti-allergic, periodontitis, etc.

The propolis is preferably comprised in an amount of 0.01 to 0.5% by weight, more preferably 0.05 to 0.2% by weight, based on the total weight of the composition of the present invention.

The monk fruit (Momordica grosvenori Swingle/Siraitia grosvenorii) is a fruit of gourd, which is a perennial plant that grows only in the highlands of Guilin, Guangxi Province, China. In China, since about 300 years ago, it has been used for a natural sweetener, prevention of various adult diseases, anticancer effects, treatment of diseases such as laryngitis, sore throat, dry cough, etc. The monk fruit is a natural sweetener, most similar to sugar, and is known to be a non-glycoside and to be incapable of being used as a nutritional source for periodontal disease bacteria. In addition, the monk fruit is highly utilized as a natural sweetener because it is not absorbed by the body and is discharged, and thus has few calories and does not increase a glycemic index.

In addition, the main active ingredients of the monk fruit are triterpenoid saponin and flavonoid glycosides. According to a pharmacological study, it was confirmed that the monk fruit has hypoglycemic, improved hyperlipidemia, antioxidant, antimutagenic, vascular permeability inhibition, antitussive and expectorant effects.

In the present invention, the monk fruit may be used in the form of an extract or a powder of the extract.

The monk fruit may be comprised in an amount of 0.01 to 0.5% by weight, more preferably 0.1 to 0.3% by weight based on the total weight of the composition of the present invention. In the present invention, by using a small amount of the monk fruit, which has a sweetness of 300 times that of sugar, it is possible to provide an oral cleaning composition having low calories and excellent antibacterial activity while improving consumer preference.

According to an embodiment of the present invention, the composition of the present invention may have a formulation in the form of a tablet. The formulation may be formed by using a tablet formulation manufacturing technique generally used in the art, and, for example, a mixed powder may be tableted with a tablet press to form a tablet form. It is desirable to tablet at high pressure and low speed in order to mold a tablet form which does not fall and break.

In the present invention, before the mixed powder is prepared into a tablet form, filtering step is performed using a sieve. In this case, a size of the sieve may affect the tablet formulation. For example, if the size of the sieve is more than 30 mesh and the filtering is very fine, the flowability and fluidity of the raw material may be affected during the tableting process, so that the binding force of the tablet may be very weak during the high pressure process. Therefore, in order to improve the binding force of the tablet, it is desirable to adjust the size of the sieve to 18 mesh or less.

In the present invention, when prepared into a tablet form formulation, an excipient for improving the binding force of the tablet may be added. As the excipient, magnesium stearate, silicon dioxide or the like may be used, and both are preferably used.

The excipient may be comprised in an amount of 0.1 to 10% by weight, more preferably 0.5 to 5% by weight, and most preferably 1.5 to 2.5% by weight based on the weight of the total composition.

According to a preferred embodiment of the present invention, when the oral cleaning composition of the present invention is prepared in a tablet form, the composition of the present invention preferably comprises: 3 to 10% by weight of salt, 40 to 70% by weight of xylitol, 0.1 to 15% by weight of bellflower, 0.1 to 15% by weight of quince, 5 to 20% by weight of mint, 1 to 20% by weight of lemon, 5 to 20% by weight of green tea, 0.01 to 0.5% by weight of propolis, 0.01 to 0.5% by weight of monk fruit, 0.1 to 5% by weight of magnesium stearate, and 0.1 to 5% by weight of silicon dioxide.

More preferably, the tablet type oral cleaning composition of the present invention may comprise: 4 to 7% by weight of salt, 45 to 60% by weight of xylitol, 0.5 to 2.0% by weight of bellflower, 0.2 to 2.0% by weight of quince, 10 to 15% by weight of mint, 5 to 15% by weight of lemon, 10 to 17% by weight of green tea, 0.05 to 0.2% by weight of propolis, 0.1 to 0.3% by weight of monk fruit, 0.5 to 1.5% by weight of magnesium stearate, and 0.5 to 1.5% by weight of silicon dioxide.

Most preferably, the tablet type oral cleaning composition of the present invention may comprise: 4.5 to 5% by weight of salt, 55 to 60% by weight of xylitol, 0.7 to 1.3% by weight of bellflower, 0.3 to 0.7% by weight of quince, 13 to 14% by weight of mint, 8 to 10% by weight of lemon, 11 to 13% by weight of green tea, 0.05 to 0.2% by weight of propolis, 0.1 to 0.3% by weight of monk fruit, 0.8 to 1.2% by weight of magnesium stearate, and 0.8 to 1.2% by weight of silicon dioxide. In the examples of the present invention, it was confirmed that the tablet type oral cleaning composition having the above compositional ratio inhibited an activity of harmful bacteria, preserved a viability of beneficial bacteria, and had very excellent efficacy particularly in inflammation induction and bad breath tests.

In addition, according to another embodiment of the present invention, when preparing a powder type oral cleaning composition, it may further comprise an anti-caking agent for preventing caking.

Maltodextrin may be used as the anti-caking agent, and it is preferable to use 1 to 5% by weight, and more preferably 2 to 4% by weight, based on the weight of the total composition.

According to a preferred embodiment of the present invention, when the oral cleaning composition of the present invention is prepared in a powder form, the composition of the present invention preferably comprises: 4.5 to 5.0% by weight of salt, 45 to 50% by weight of xylitol, 8 to 12% by weight of bellflower, 8 to 12% by weight of quince, 10 to 12% by weight of mint, 3 to 7% by weight of lemon, 5 to 10% by weight of green tea, 0.01 to 0.5% by weight of propolis, 0.1 to 0.3% by weight of monk fruit, and 2 to 4% by weight of maltodextrin.

Since the tablet or powder type oral cleaning composition according to the present invention is composed of natural ingredients and contains no chemical components, it can be ingested as it is without spitting it out after use, and therefore, can be used conveniently.

In addition, the tablet or powder type oral cleaning composition of the present invention can inhibit harmful bacteria in an oral cavity such *Streptococcus constellatus*, *Streptococcus sanguinis*, *Streptococcus mutans*, *Eikenella corrodens*, *Fusobacterium nucleatum*, *Streptococcus sobrinus*, *Aggregatibacter actinomycetemcomitans*, *Porphyromonas gingivalis*, *Prevotella nigrescens*, *Prevotella intermedia*, etc., thereby improving dental caries and periodontal disease.

In addition, the oral cleaning composition of the present invention has a lower inhibition rate of beneficial bacteria such as *Lactobacillus salivarius* and *Streptococcus salivarius* than conventional products, and thus, has a characteristic of inhibiting harmful bacteria while allowing beneficial bacteria to survive.

In addition, the oral cleaning composition of the present invention can remove volatile compounds such as hydrogen sulfide, methyl mercaptan and dimethyl sulfide, which are a main cause of bad breath; amines such as butylric acid and cadaverine; and polyphenolic compounds such as indole and pyridine. In one example of the present invention, it was confirmed that the oral cleaning composition of the present invention can substantially significantly reduce components of ammonia, formaldehyde, trimethylamine and methylmercaptan.

Lastly, the oral cleaning composition of the present invention can be ingested without a feeling of rejection by selecting an optimal ratio which can display the taste suitable for the consumer's taste, while exhibiting the effects of inhibiting bacteria in the oral cavity and reducing bad breath.

EXAMPLES

Hereinafter, the present invention will be described in more detail by way of examples. It will be apparent to those of ordinary skill in the art that these examples are intended only to illustrate the present invention, and the scope of the present invention is not to be construed as being limited by the examples.

Preparation for Experiment

A composition for oral cleaning was prepared in the compositional shown in Table 1 below. Each component was prepared in the form of an extract powder, and in the case of a tablet formulation, it was prepared by tableting with a tablet press.

For a comparative experiment, bellflower extract powder (*Platycodon grandiflorum*), quince extract powder (*Chaenomeles sinensis* Koehne) and monk fruit extract powder (*Siraitia grosvenorii*) were tested as Comparative Examples 1 to 3, respectively, and for comparison with commercial products, liquid oral cleaning products of D company and J company were used as Comparative Examples 4 and 5, respectively, the results were compared.

In the experiment, the powdered sample was dissolved at a level of 100 mg/mL, and was used after 0.45 μm filtering.

TABLE 1

| Formulation | Example 1 Powder type | Example 2 | Example 3 Tablet type | Example 4 | Example 5 |
|---|---|---|---|---|---|
| Enzyme salt | 4.8 | 7.0 | 4.8 | 5.0 | 4.8 |
| Xylitol | 47.0 | 57.2 | 57.0 | 46.0 | 48.0 |
| Bellflower | 10.0 | 0.7 | 1.0 | 1.2 | 1.2 |
| Quince | 10.0 | 0.2 | 0.5 | 0.5 | 0.5 |
| Mint | 11.0 | 13.0 | 13.4 | 14.0 | 14.0 |
| Maltodextrin | 3.0 | — | — | — | — |
| Magnesium stearate | — | 0.8 | 1.0 | 1.0 | 1.0 |
| Silicon dioxide | — | 0.8 | 1.0 | 1.0 | 1.0 |
| Lemon | 0.5 | 8.0 | 9.0 | 14.0 | 14.0 |

TABLE 1-continued

| Formulation | Example 1 Powder type | Example 2 | Example 3 Tablet type | Example 4 | Example 5 |
|---|---|---|---|---|---|
| Green tea | 9.0 | 12.0 | 12.0 | 17.0 | 15.2 |
| Propolis | 0.1 | 0.1 | 0.1 | 0.1 | 0.1 |
| Monk fruit | 0.1 | 0.2 | 0.2 | 0.2 | 0.2 |
| Total | 100 | 100 | 100 | 100 | 100 |

Experimental Example 1: pH Measurement

A total of 10 samples of Examples 1 to 5 and Comparative Examples 1 to 5 were dispensed into a 15 mL conical tube by 5 mL. Three tubes for each sample were measured 6 times with a pH meter. The results are shown in FIG. 1.

In FIG. 1, it was confirmed that in the case of Examples 2 to 5, which are a tablet type compositions of the present invention, the pH was in the range of 4.0 to 4.2, which is similar to those of Comparative Examples 4 and 5, which are commercial products, 4.7 and 4.2.

In the case of Example 1, which is a powder type composition, the pH was 3.4, indicating a rather low value.

The bellflower and quince extracts, which are natural extracts, exhibited pH 4.6 and 3.2, respectively, but the monk fruit extract showed a basicity of pH 8.6.

color was calculated and quantified using the black & white threshold, and then quantitatively evaluated.

The results of the antibacterial experiment for each sample are shown in FIGS. 2 to 13, and the results are summarized and shown in Table 3 below.

TABLE 2

| Kind | Bacteria | Culture medium |
|---|---|---|
| Harmful bacteria | Streptococcus constellatus | Tryptic Soy agar |
| | Streptococcus sanguinis | Rabbit blood agar |
| | Streptococcus mutans | Brain Heart infusion agar |
| | Streptococcus constellatus | Tryptic Soy agar |
| | Eikenella corrodens | Brain Heart infusion agar |
| | Fusobacterium nucleatum | Brain Heart infusion agar |
| | Streptococcus sobrinus | Brain Heart infusion agar |
| | Aggregatibacter actinomycetemcomitans | Brain Heart infusion agar |
| | Porphyromonas gingivalis | Tryptic Soy agar |
| | Prevotella nigrescens | Tryptic Soy agar |
| | Prevotella intermedia | Tryptic Soy agar |
| Beneficial bacteria | Streptococcus salivarius | Corynebacterium agar |
| | Lactobacillus salivarius | MRS agar |

TABLE 3

| | | comparative Example 1 | comparative Example 2 | comparative Example 3 | Example 1 | Example 2 | Example 3 | Example 4 | Example 5 | comparative Example 4 | comparative Example 5 |
|---|---|---|---|---|---|---|---|---|---|---|---|
| Harmful bacteria | S. constellatus | 80 | 81 | 87 | 96 | 88 | 82 | 79 | 79 | 94 | 90 |
| | S. sanguinis | 94 | 99 | 93 | 94 | 94 | 91 | 96 | 94 | 92 | 90 |
| | S. mutans | 95 | 95 | 92 | 81 | 94 | 92 | 93 | 92 | 93 | 98 |
| | S. constellatus | 81 | 91 | 93 | 97 | 91 | 83 | 92 | 86 | 91 | 94 |
| | E. corrodens | 93 | 94 | 94 | 95 | 96 | 97 | 95 | 91 | 94 | 86 |
| | F. nucleatum | 96 | 98 | 93 | 93 | 92 | 88 | 90 | 93 | 93 | 91 |
| | S. sobrinns | 81 | 88 | 95 | 89 | 83 | 92 | 85 | 89 | 95 | 96 |
| | A. actinomycetemcomitans | 78 | 94 | 86 | 95 | 90 | 80 | 84 | 80 | 96 | 92 |
| | P. gingivalis | 69 | 88 | 86 | 81 | 60 | 76 | 77 | 75 | 95 | 90 |
| | P. nigrescens | 89 | 97 | 94 | 96 | 94 | 89 | 90 | 96 | 95 | 92 |
| | P. intermedia | 93 | 91 | 91 | 84 | 97 | 94 | 92 | 99 | 92 | 88 |
| Beneficial bacteria | S. salivarius | 11 | 27 | 28 | 10 | 22 | 22 | 22 | 27 | 90 | 18 |
| | L. salivarius | 44 | 40 | 35 | 86 | 39 | 38 | 39 | 44 | 86 | 77 |

Experimental Example 2: Antibacterial Experiment

Antibacterial experiments were performed on 11 pathogenic oral microorganisms (hereinafter, "harmful bacteria") and 2 non-pathogenic microorganisms (hereinafter, "beneficial bacteria") of Table 2 below.

The harmful and beneficial bacteria were cultured for 48 hours in a shaker at 36.5° C. and 145 rpm in 5 mL of broth liquid medium. 100 CFU harmful bacteria and beneficial bacteria were spread on a 60∅ culture dish, and cultured for 24 hours in an incubator at 37° C. and 5% $CO_2$.

After placing 4 8 mm paper discs (ADVENTEC paper disc for antibiotic assay) on a culture dish, 100 uL of the test sample was applied to the paper disc.

At 24 hours after applying the sample, the culture dishes were photographed and the effect of inhibiting microbial enhancement according to the threshold value was observed. As for the evaluation method, a range in the medium was set using Image J Program, and the area of the dots in the white As can be seen from the above tables, all of the compositions of Examples 1 to 5 showed an antibacterial activity against the harmful bacteria, which is not significantly lower or is more superior compared to Comparative Examples 4 and 5, which are the commercial products.

In addition, with regard to the inhibition of the beneficial bacteria, the commercial products of Comparative Examples 4 and 5 were found to inhibit the beneficial bacteria as well, but in the case of Examples 1 to 5 using natural extracts, it was confirmed that the beneficial bacteria were not significantly inhibited, and therefore, the beneficial bacteria can be maintained while inhibiting the harmful bacteria.

In the case of Example 1 of the powder type formulation, the viability of S. salivarius was largely preserved, but the viability of L. salivarius was shown to be largely inhibited. However, in the case of Examples 2 to 5 of the tablet formulation, the viability of both beneficial bacteria was well preserved.

Experimental Example 3: Anti-Inflammatory Experiment

3-1. Cell Viability Test

In a T75 flask, 27 passages, Raw 264.7 cells were generally cultured. The Raw 264.7 cells were subjected to cell stabilization through subculture within 3 times, and then cultured in a 96 well culture plate at $1\times10^4$ cells/mL for 2 hours.

After treated with 1 µg/mL Lipopolysaccharides and cultured for 24 hours, 100 µl of each of the samples of Examples and Comparative Examples was injected at 100 mg/mL, respectively, and cultured for 24 hours.

Figure 14:
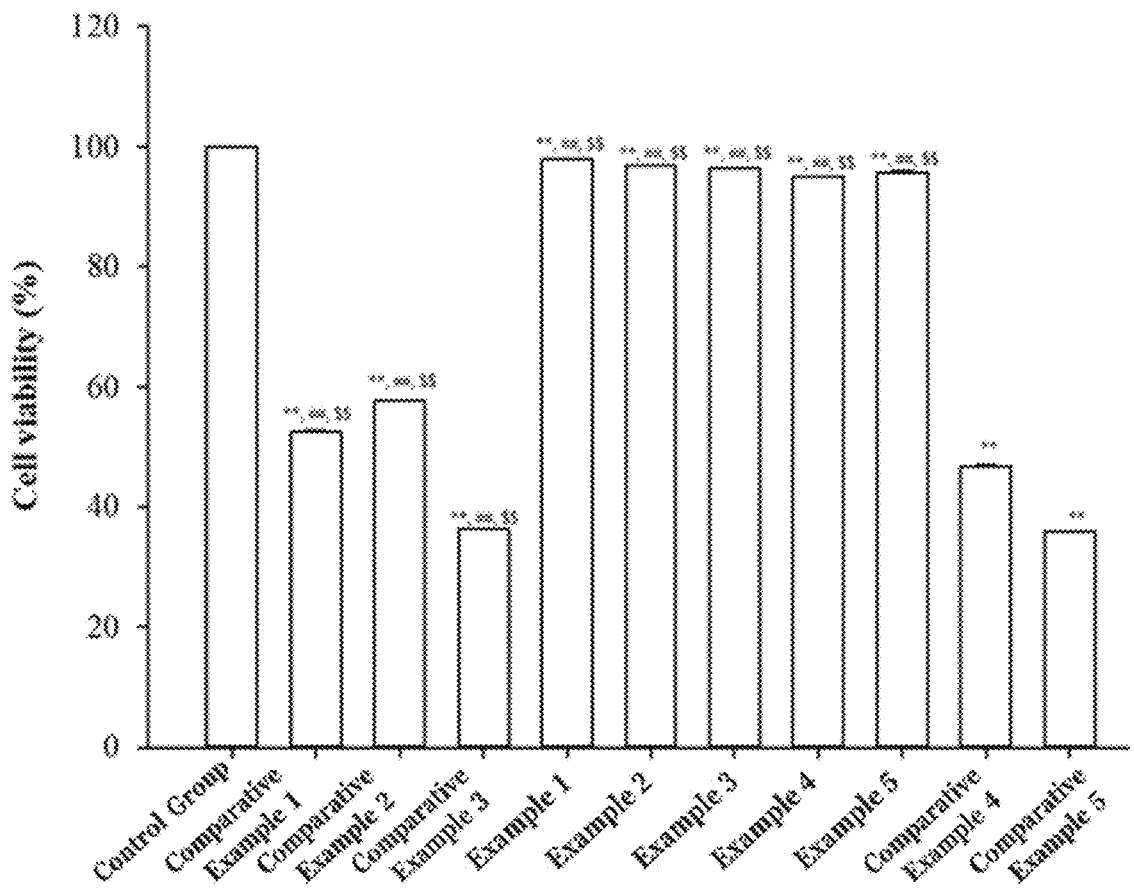
FIG. 14 shows cell viability for samples of Examples and Comparative Examples.

After injecting a MTT assay kit (Dojindo, Cell Counting Kit-8) into each well and re-culturing them for 2 hours in an incubator under 37° C./5% $CO_2$ environment, the cell viability was measured at 450 nm absorbance, and the results are shown in FIG. 14.

In FIG. 14, it can be seen that all of the compositions of Examples 1 to 5 exhibited a value close to 100% cell viability and thus had very low toxicity. These results are compared to the very low cell viability of the commercial products of Comparative Examples 4 and 5, 46.7% and 35.9%, respectively.

In addition, in the case of Comparative Examples 1 to 3, which are natural extract powders, the cell viability was low even though no toxicity was reported. This is judged to be a problem that occurred in the process of extracting and powdering the natural products. In the case of the composition of the present invention, it can be seen that this problem is completely overcome.

3-2. NO Assay Test

In order to confirm the NO inhibitory effect, a sample in which NO was generated by LPS was treated with the oral cleaning compositions of Examples and Comparative Examples to confirm the NO generation and elimination effects.

In a T75 flask, 27 passages, Raw 264.7 cells were generally cultured. The Raw 264.7 cells were subjected to cell stabilization through subculture within 3 times, and then cultured in a 96 well culture plate at $1\times10^4$ cells/mL for 2 hours.

After treated with 1 µg/mL Lipopolysaccharides and cultured for 24 hours, 100 µl of each of the samples of Examples and Comparative Examples was injected at 100 mg/mL, respectively, and cultured for 24 hours.

100 mL of media in each well was collected and transferred to a 96 well culture plate, and then measured at 540-550 nm absorbance by using a NO assay kit (Cayman, nitrate colorimetric assay kit). The measurement results are shown in FIG. 15.

Figure 15:
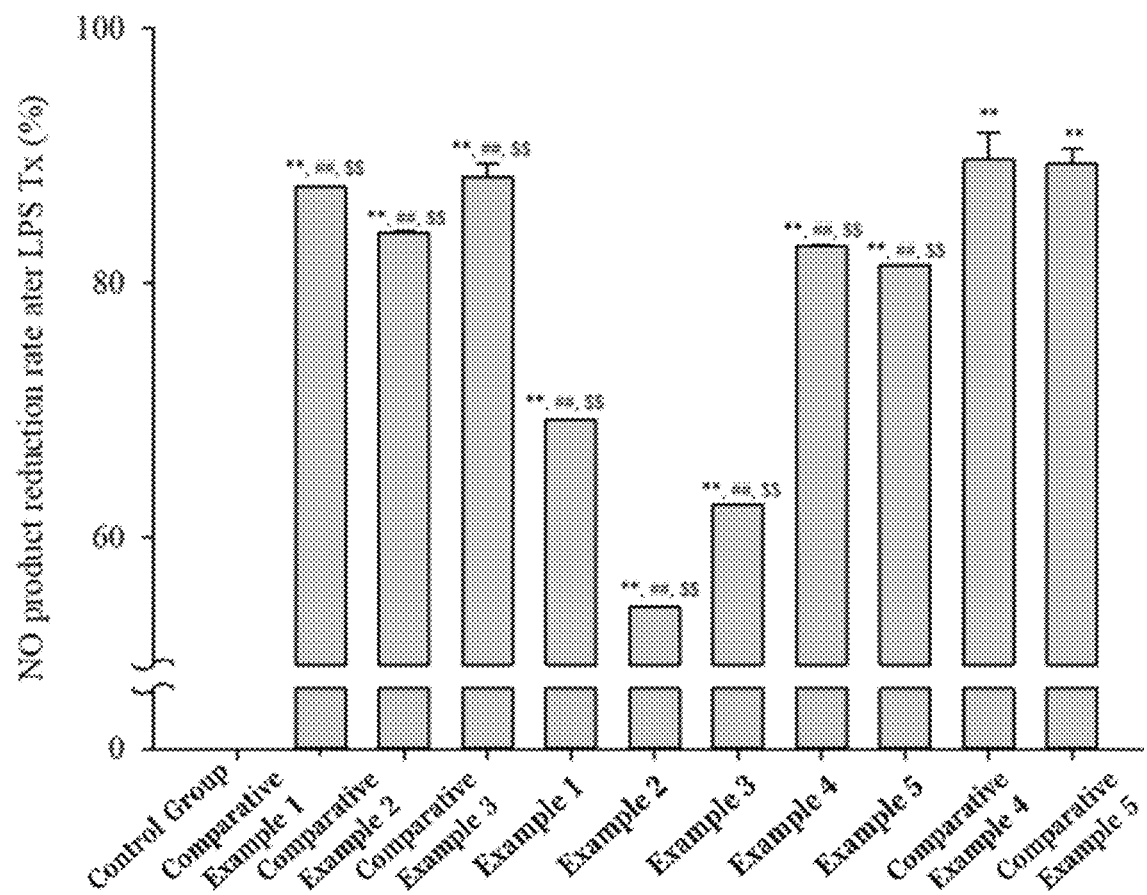
FIG. 15 is a result of analyzing the amount of NO production in cells to which samples of Examples and Comparative Examples were applied after LPS treatment.

In FIG. 15, it was observed that all samples were statistically significantly effective in inhibiting NO production compared to the control group. When the inhibition of NO production of the control group treated with LPS was viewed as 0%, it was observed that all samples inhibited the NO production by an average of 79%.

In particular, Examples 4 and 5 showed a level of NO reduction similar to that of Comparative Example 2, which is a commercial product, and showed an inhibition level of 80% or more.

3-3. Analysis of Protein Expression Related to Inflammation

A protein concentration in the culture supernatant was measured by using Tumor necrosis factor-alpha (TNF-α), Interleukin-1 beta (IL-1β) and Interleukin-6 (IL-6), which are cytokines related to inflammation, and a murine inflammatory cytokine pre-coated ELISA kit.

After cell stabilization was carried out by subculturing Raw 264.7 cells on a 100 mm dish plate within 3 times, the cells were cultured in a 96 well culture plate at $1\times10^4$ cells/mL for 2 hours.

The cells were 300 µM treated with sodium nitroprusside (SNP), which has been studied to be concerned with inflammation because it produces NO and causes oxidative stress, and cultured for 16 hours, and then the Example was injected at a concentration of 2 to 20 mg/mL and cultured for 24 hours.

Then, 50 µl of an assay dilution was added to each of the provided well; 50 µl of each of standard solution and test solution for the respective cytokines were added to the center of the well; and the plate was lightly beaten on the floor so that they can be well mixed, and then, the wells were covered with a provided sealing tape and allowed to react at room temperature for 2 hours.

The sealing tape was removed, the washing process was repeated 5 times with a provided washing buffer, and 100 µl of a conjugate solution of the cytokine to be measured was added to each well, which is covered with a sealing tape and allowed to react for 2 hours. Then, the washing process was repeated 5 times with the washing buffer.

100 µl of a substrate solution was added to each well, which is allowed to react while being kept in a light-shielding state at room temperature for 30 minutes. Then, 100 µl of a stop solution was added to each well, which was measured at 450 nm with a microplate reader within 30 minutes.

Figure 16A:
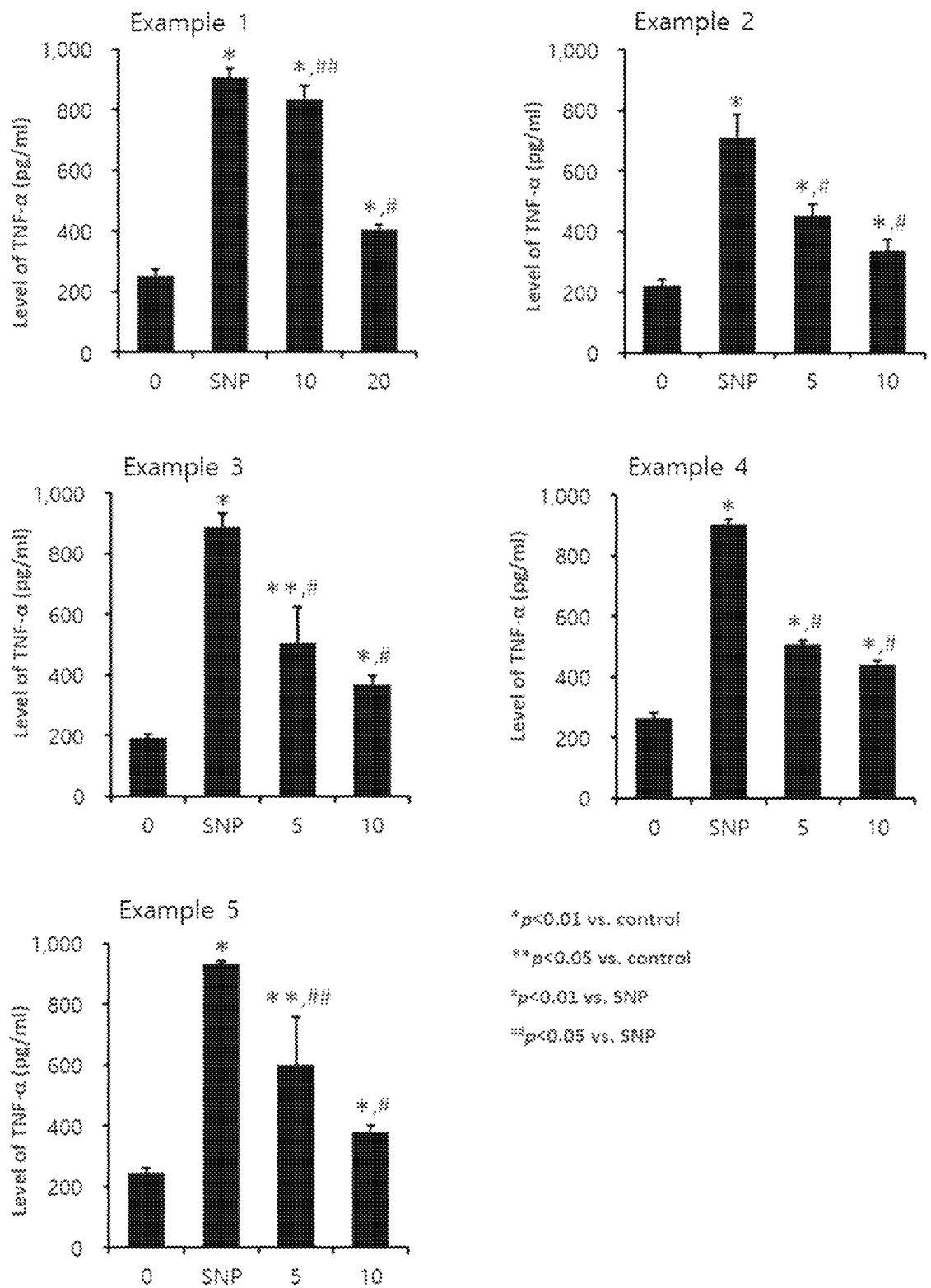
FIG. 16A shows a result of measuring an expression level of TNF-α according to the Examples.

FIG. 16A shows the result of measuring an expression level of TNF-α according to the Example.

The TNF-α is mainly produced in mononuclear cells and macrophages; and is an inflammation induction mediating cytokine which induces immune and inflammatory responses, and is involved in functions such as cell growth and differentiation, apoptosis and necrosis, and increases vascular permeability.

In the case of Example 1, it was confirmed that the amount of TNF-α production increased due to the SNP used as a positive control showed a statistically significant reduction effect when each sample is treated with 10 and 20 mg/ml, In the case of Examples 2 to 5, it was confirmed that the amount of TNF-α production increased due to the SNP used as a positive control showed a statistically significant reduction effect when each sample is treated with 5 and 10 mg/ml.

Figure 16B:
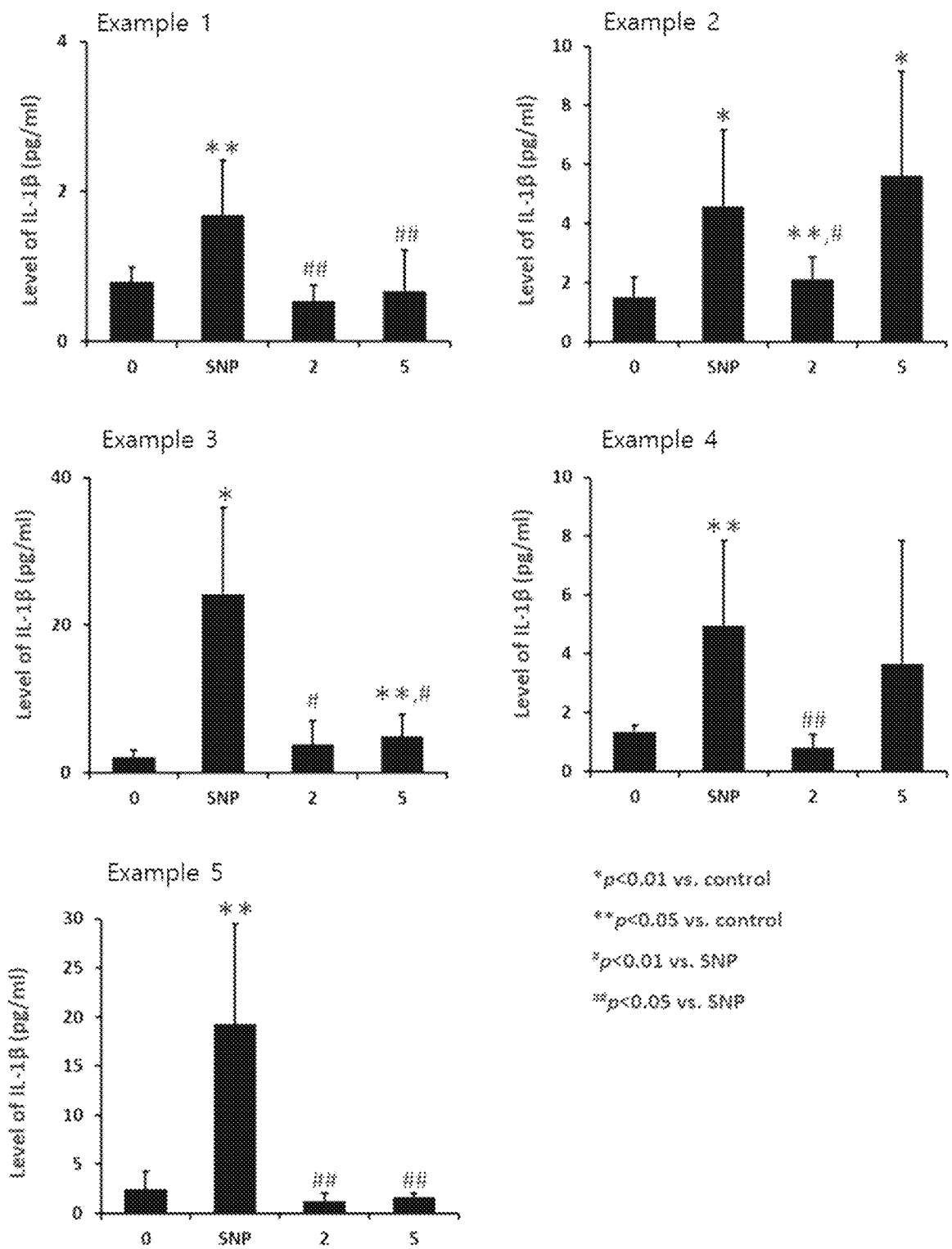
FIG. 16B shows a result of measuring an expression level of IL-1β according to the Examples.

FIG. 16B shows the result of measuring an expression level of IL-1β according to the Examples.

Similar to TNF-α, Interleukin-1 (IL-1) is a mediator of the host's inflammatory response to infection or other stimuli, and is produced in various cells such as monocytes, macrophages, keratinocytes, NK cells, T cells, B cells and endothelial cells through stimulation of various production-inducing substances.

In FIG. 16B, in the case of Examples 1, 3 and 5, the amount of IL-1β production increased due to SNP was significantly reduced at both 2 and 5 mg/ml, especially in the case of Example 5, it was confirmed that the amount of IL-1β production was significantly reduced to the control level at both 2 and 5 mg/ml concentrations.

In the case of Examples 2 and 4, it was confirmed that the amount of IL-1β production increased due to SNP was significantly reduced when treated with 2 mg/ml, but at 5 mg/ml, it was confirmed that there was no reduction or only a small reduction.

Figure 16C:
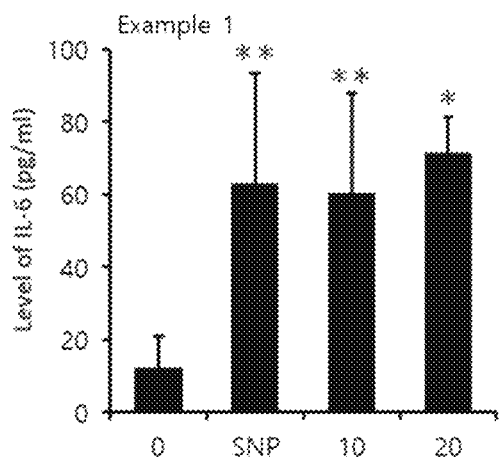
FIG. 16C shows a result of measuring an expression level of IL-6 according to the Examples.
Figure 16C:
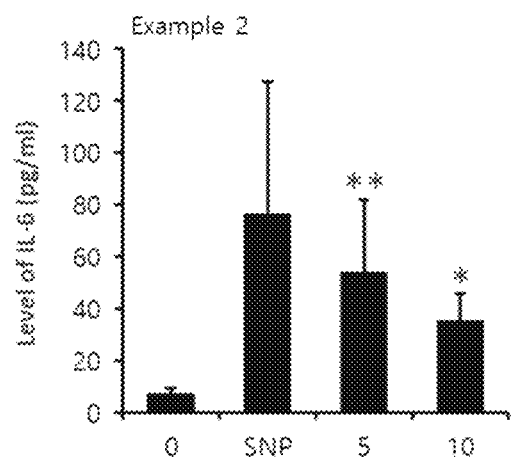
Figure 16C:
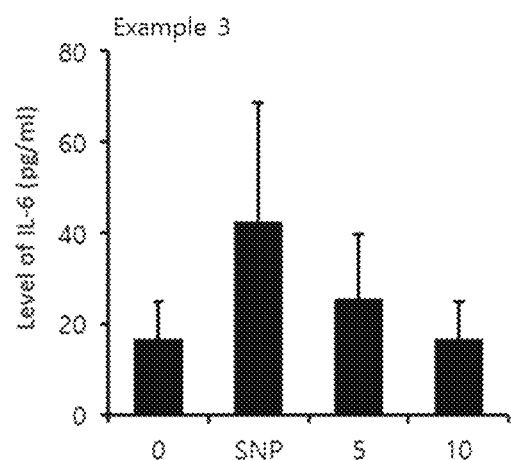
Figure 16C:
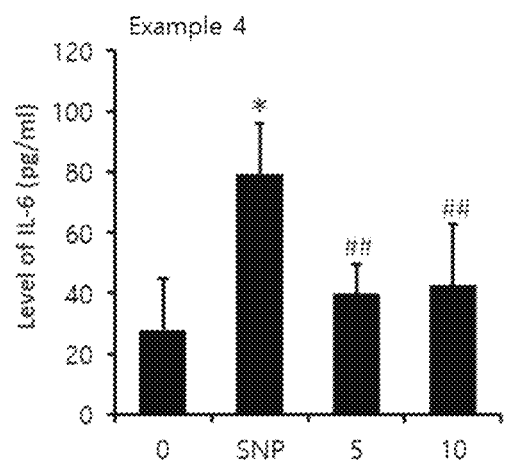
Figure 16C:
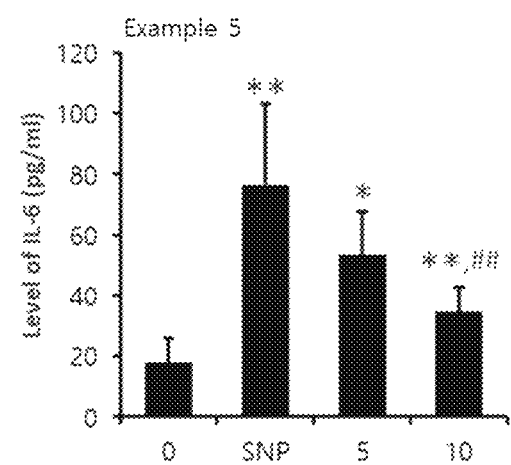

FIG. 16C shows the result of measuring an expression level of IL-6 according to the Examples.

The Interleukin-6 (IL-6) is produced by macrophages and T-cells, and is known to be a derivative of acute protein reaction along with TNF-α and IL-1 and to be a pro- and anti-inflammatory cytokine.

In FIG. 16c, in the case of Example 1, the amount of IL-6 production increased due to SNP did not show a reduction effect at the level of 10 and 20 mg/ml, but in the case of Examples 2 to 5, it was confirmed that the amount of IL-6 production increased due to SNP was reduced, and in the case of Example 4, it was confirmed that the amount of IL-6 production increased due to SNP was significantly lowered to the Control level.

Experimental Example 4: Bad Breath Test 4-1. $H_2S$ Solution Test

In order to assume the conditions (150-200 ppb) causing physiological and pathological bad breath, an $H_2S$ solution was used to conduct an experiment for inhibiting the occurrence of bad breath.

A stock solution of the $H_2S$ solution and third distilled water were diluted in a ratio of 1:1000 and set as a control group.

Figure 17:
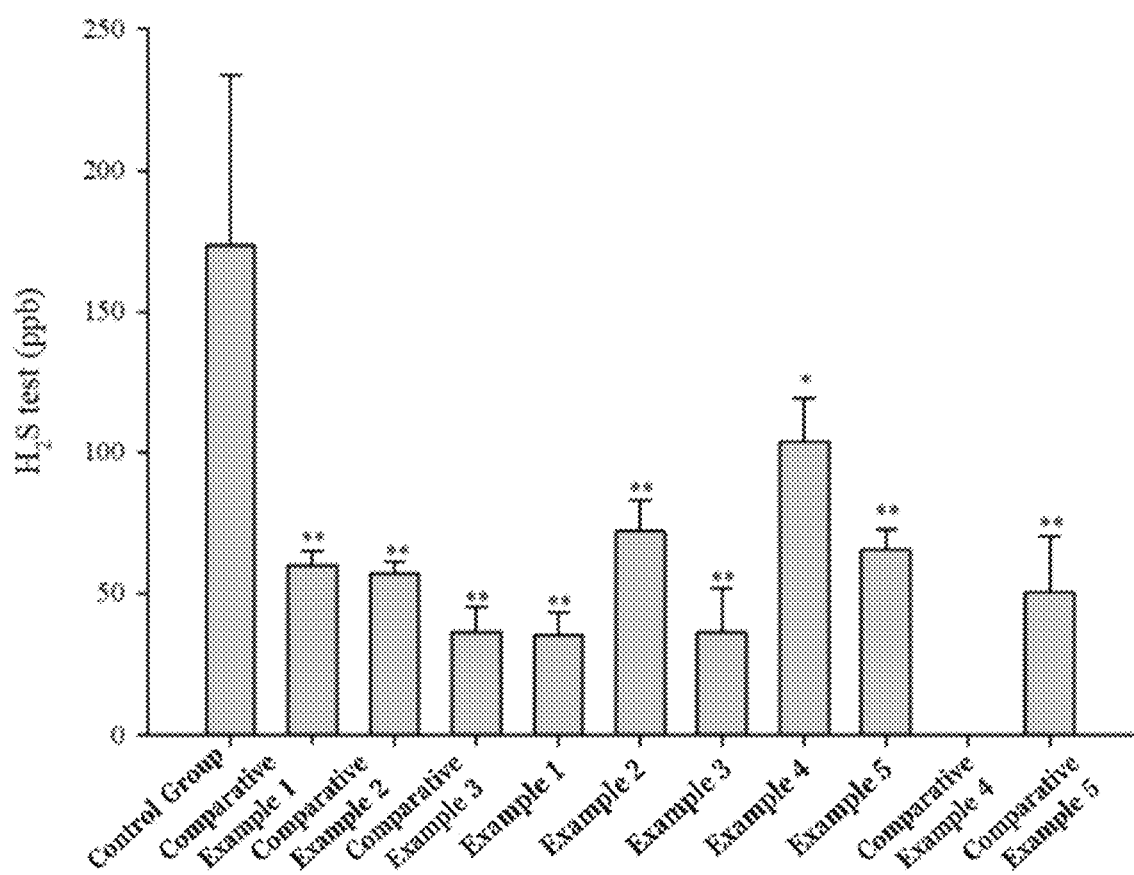
FIG. 17 shows a test result of a $H_2S$ solution for samples of Examples and Comparative Examples.

The third distilled water and 10 mL of each of the samples of Examples and Comparative Examples were placed in a 50 mL conical tube, and then 1 μl of the 1:1000 diluted $H_2S$ solution was added. $H_2S$ concentration was measured three times for all samples to determine the bad breath-inhibiting ability. The results are shown in FIG. 17.

The 1000-fold diluted $H_2S$ solution was measured at 120-290 ppb.

All samples of Examples 1 to 5 of the present invention were observed to have an $H_2S$ improvement effect of 79.6%, 58.4%, 79.1%, 39.9% and 62.5%, respectively, compared to the control group.

In the case of Comparative Example 4, which is a commercial product, $H_2S$ was not measured even in a number of experiments, whereas in the case of Comparative Example 5, an improvement effect of 71.1% was observed, which confirms that the sample of the present invention has a bad breath inhibiting effect similar to or better than that of the commercial product.

4-2. Bad Breath Removal Test Using Gas Detection Tube Method

It was attempted to confirm the bad breath inhibitory efficacy of the oral cleaning composition of the present invention using a gas detection tube method applying the standard test method of ASTM D1988-06 (ASTM D1988-06, 2011).

A 500 mL sealable container was prepared by fitting a rubber stopper through which a detection tube can be accessed, and an odor test solution described in Table 4 below was injected into the container to induce an odor for 30 minutes.

As an oral cleaning sample, the samples of Example 3 of the tablet formulation and Example 1 of the powder type formulation which showed the best performance in the previous experiment were used.

10 mg/mi of the samples were injected 30 minutes after the occurrence of odor, respectively, and after 60 minutes, the residual gas was compared using a gas detector (GV-100S). The experiment was carried out in a fume hood, and the conditions of temperature and humidity were set to 21-23° C. and 40-55%.

When an initial value of each odor component before treated with the oral cleaning of the present invention is considered as 100%, the value of the odor component measured after 60 minutes is as shown in Table 4 below.

TABLE 4

| | | | Odor component (%) after 60 minutes | |
|---|---|---|---|---|
| | Color change | Characteristic | Example 1 (Powder type) | Example 3 (Tablet type) |
| Ammonia | Purple → Yellow | Irritating smell, Fermented skate | 71 | 68 |
| Formaldehyde | White → Brown | Cigarette smoke component, Main culprit of sick house syndrome, Stinging and choking odor | 62 | 61 |
| Trimethylamine | Pink → Yellow | Designation of odor substances, Sulfur compounds causing bad breath or odor when food is rotted, By-products produced by the action of bacteria acting on saliva or proteins or peptides in food in the mouth, Smells like rotten cabbage | 56 | 54 |
| Methyl mercaptan | White → Yellow | Sweat and odorous substances from a mouth, Smell of rotting fish, Main component of fish odor syndrome. | 12 | 15 |

From the above table, it was confirmed that both the powder type and tablet type compositions of Examples 1 and 3 exhibited a odor reduction effect of about 10 to 70%, and that on average, about 50% of bad breath could be removed.

The specific parts of the contents of the present invention have been described in detail above. It will be apparent to those of ordinary skill in the art that these specific descriptions are only preferred embodiments, and the scope of the present invention is not limited thereby. Accordingly, it will be said that the substantial scope of the present invention is defined by the appended claims and their equivalents.

What is claimed is:

1. A tablet or powder oral cleaning composition comprising: 3 to 10% by weight of salt, 40 to 70% by weight of xylitol, 0.5 to 15% by weight of bellflower, 0.1 to 15% by weight of quince and 10 to 15% by weight of mint, based on the weight of the total composition, wherein the salt is an enzyme salt comprising a fermented wild grass juice, said fermented wild grass juice containing an enzyme.

2. The tablet or powder oral cleaning composition of claim 1, further comprising: 1 to 20% by weight of lemon, 5 to 20% by weight of green tea, 0.01 to 0.5% by weight of propolis and 0.01 to 0.5% by weight of monk fruit, based on the weight of the total composition.

3. The tablet or powder oral cleaning composition of claim 1, further comprising: 0.1 to 5% by weight of magnesium stearate and 0.1 to 5% by weight of silicon dioxide, based on the weight of the total composition, and wherein the composition is a tablet formulation.

4. The tablet or powder oral cleaning composition of claim 1, further comprising: 1 to 5% by weight of maltodextrin based on the weight of the total composition, and wherein the composition is a powder formulation.

5. A method for suppressing oral malodor, comprising applying to oral cavity the composition of claim 1.

6. A method of inhibiting growth of bacteria in oral cavity of a subject, comprising applying to the oral cavity the composition of claim 1.

7. A method for suppressing oral malodor, comprising applying to oral cavity the composition of claim 2.

8. A method for suppressing oral malodor, comprising applying to oral cavity the composition of claim 3.

9. A method for suppressing oral malodor, comprising applying to oral cavity the composition of claim 4.

10. A method of inhibiting growth of bacteria in oral cavity of a subject, comprising applying to the oral cavity the composition of claim 2.

11. A method of inhibiting growth of bacteria in oral cavity of a subject, comprising applying to the oral cavity the composition of claim 3.

12. A method of inhibiting growth of bacteria in oral cavity of a subject, comprising applying to the oral cavity the composition of claim 4.

13. The tablet or powder oral cleaning composition of claim 1, wherein the enzyme is protease, lipase, amylase, cellulase, SOD (superoxide dismutase), or a combination thereof.

* * * * *